(12) United States Patent
Coates et al.

(10) Patent No.: US 10,377,850 B2
(45) Date of Patent: Aug. 13, 2019

(54) POLYESTER STEREOCOMPLEXES, COMPOSITIONS COMPRISING SAME, AND METHODS OF MAKING AND USING SAME

(71) Applicant: Cornell University, Ithaca, NY (US)

(72) Inventors: Geoffrey Coates, Lansing, NY (US); Julie Whitehead, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/502,234

(22) PCT Filed: Aug. 13, 2015

(86) PCT No.: PCT/US2015/044984
§ 371 (c)(1),
(2) Date: Feb. 7, 2017

(87) PCT Pub. No.: WO2016/025675
PCT Pub. Date: Feb. 18, 2016

(65) Prior Publication Data
US 2017/0226283 A1  Aug. 10, 2017

Related U.S. Application Data

(60) Provisional application No. 62/036,807, filed on Aug. 13, 2014.

(51) Int. Cl.
| | | |
|---|---|---|
| *C08G 63/00* | (2006.01) | |
| *C08G 63/16* | (2006.01) | |
| *C08L 67/02* | (2006.01) | |
| *A61L 27/18* | (2006.01) | |
| *A61L 29/06* | (2006.01) | |
| *A61L 31/06* | (2006.01) | |
| *A61L 15/26* | (2006.01) | |
| *A61K 47/34* | (2017.01) | |

(52) U.S. Cl.
CPC .............. *C08G 63/00* (2013.01); *A61L 15/26* (2013.01); *A61L 27/18* (2013.01); *A61L 29/06* (2013.01); *A61L 31/06* (2013.01); *C08G 63/16* (2013.01); *C08L 67/02* (2013.01); *A61K 47/34* (2013.01)

(58) Field of Classification Search
CPC ......... C08G 63/00; C08G 63/16; A61L 15/26; A61L 31/06; A61L 27/18; A61L 29/06; C08L 67/02; A61K 47/34
See application file for complete search history.

(56) References Cited

U.S. PATENT DOCUMENTS

| | | |
|---|---|---|
| 5,612,416 A | 3/1997 | McCollum et al. |
| 6,121,400 A | 9/2000 | Webster et al. |
| 2008/0305174 A1 | 12/2008 | Gyurik et al. |
| 2009/0005514 A1 | 1/2009 | Uradnisheck et al. |
| 2012/0322908 A1 | 12/2012 | Bastioli |

OTHER PUBLICATIONS

Angela M. DiCiccio, Geoffrey W. Coates "Ring-Opening Copolymerization of Maleic Anhydride with Epoxides: A Chain-Growth Approach to Unsaturated Polyesters", Jun. 24, 2011.*
Fischer, R.F.; Journal of Polymer Science, vol. 44, p. 155-172, 1960.*
Takenouchi, S., et al.; Polymer Journal, vol. 34, No. 1, p. 36-42, 2002.*
Robert, C., et al.; Nature Communications, p. 1-6, 2011.*
Domb, A.J., et al.; Advanced Drug Delivery Reviews, vol. 55, Issue 4, p. 549-583, 2003.*
Chemical & Engineering News, Chiral Catalyst Leads to New Stereopolymer, p. 1-2, 2014.*

* cited by examiner

*Primary Examiner* — Robert S Jones
(74) *Attorney, Agent, or Firm* — Hodgson Russ LLP

(57) ABSTRACT

Compositions comprising stereocomplexes of enantiomeric polymer chains having individual repeat units formed from the reaction of an epoxide and cyclic anhydride. The compositions can be made by mixing two types of enantiomeric polymer chains having opposite absolute stereochemistry. The compositions can be used in applications such as biomedical applications and drug delivery applications.

13 Claims, 23 Drawing Sheets

POLYESTER STEREOCOMPLEXES, COMPOSITIONS COMPRISING SAME, AND METHODS OF MAKING AND USING SAME

CROSS-REFERENCE TO RELATED APPLICATIONS

This application claims priority to U.S. provisional patent application No. 62/036,807, filed Aug. 13, 2014, the disclosure of which is incorporated herein by reference.

STATEMENT REGARDING FEDERALLY SPONSORED RESEARCH

This invention was made with government support under contract no. CHE-1413862 awarded by the National Science Foundation. The government has certain rights in the invention.

FIELD OF THE DISCLOSURE

The present disclosure generally relates to compositions comprising enantiomeric polymer chains. More particularly, the disclosure relates to compositions comprising enantiomeric polymer chains having individual repeat units formed by the reaction of an epoxide and a cyclic anhydride.

BACKGROUND OF THE DISCLOSURE

Polyethylene (PE) and isotactic polypropylene (iPP) are the two most widely produced polymers in the world, accounting for over half of the approximately 280 million tons of plastic produced in 2012. These semicrystalline polyolefins are ubiquitous because of their low cost and impressive physical and thermal properties, allowing for their use in a wide array of applications. Since the discovery of these materials in the 1950's, relatively few new classes of semicrystalline polymers have been commercialized, and even fewer where the monomers are nearly as readily available and inexpensive as ethylene and propylene.

Stereocomplexation occurs when a stereoselective interaction between two stereoregular complementary polymers in the crystalline state results in altered physical and thermal properties in comparison to the parent polymers. Most commonly, stereocomplexes are formed between enantiomerically complementary polymer strands. Stereocomplexation improves and allows for tunability of polymer properties, including crystallinity as well as biodegradability.

Epoxides have been studied in alternating copolymerizations with $CO_2$ to form polycarbonates and with cyclic anhydrides to form polyesters. In the case of propylene oxide (PO)/$CO_2$ copolymerization, even highly regio- and stereoregular polycarbonates are amorphous. However, the copolymerization of PO with cyclic anhydrides has resulted in the formation of a new class of semicrystalline polyesters. Many currently available aliphatic polyesters, including polylactic acid (PLA), and polyhydroxybutyrate (PHB), can be safely decomposed in aerobic composting environments, anaerobic landfill environments, and in vivo in the case of biomedical devices. However, commercializing many current biodegradable polyesters challenges the existing industrial infrastructure because the processes required to produce them rely partially or fully on biotechnology.

BRIEF SUMMARY OF THE DISCLOSURE

In an aspect, the present disclosure provides compositions comprised of enantiomeric polymer chains that form one or more stereocomplexes. The enantiomeric chains have repeat units formed from a ring-opening reaction of an epoxide (e.g., an enantiopure epoxide) followed by a ring-opening of a cyclic anhydride. One or more of the enantiomeric chains (e.g., one or more first enantiomeric polymer chains and/or one or more second polymer chains) may further comprise one or more small molecules and/or one or more polymeric chains.

One or more of the enantiomeric chains (e.g., one or more first enantiomeric polymer chains and/or one or more second polymer chains) may be a random copolymer. The enantiomeric chain(s) include one or more additional repeat units (in addition to Repeat Unit Structures I and/or II).

The composition may comprise enantiomeric polymer chains comprising blocks of individual repeat units having opposite absolute stereochemistry. The enantiomeric polymer chains are stereoblock copolymers.

For example, the compositions comprise a new polymer stereocomplex formed from the mixture of racemic, isotactic, regioregular chains of poly((S)-propylene succinate) and poly((R)-propylene succinate) synthesized via the alternating copolymerization of propylene oxide and succinic anhydride. While the parent polymers [of poly((S)-propylene succinate) or of poly((R)-propylene succinate)] crystallize very slowly and exhibit a melting temperature around 79° C., the stereocomplex comprising both crystallizes very quickly and exhibits a melting temperature up to 120° C., comparable to that of low density polyethylene. However, unlike polyethylene, this stereocomplex of poly(propylene succinate) allows a biodegradable, biorenewable and biocompatible polyester, potentially enabling its use in a wide variety of applications, e.g. for biomedical or drug delivery applications.

In an embodiment, a composition comprises: polymer chains that form one or more stereocomplexes, where the polymer chains comprise i) first enantiomeric polymer chains having a first enantiomeric structure that comprise individual repeat units having the following structure:

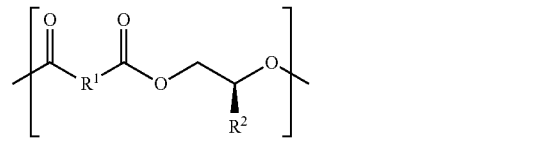

(Repeat Unit Structure I)

and second enantiomeric polymer chains having a second enantiomeric structure that is the opposite absolute stereochemistry of the first enantiomeric structure that comprise individual repeat units having the following structure:

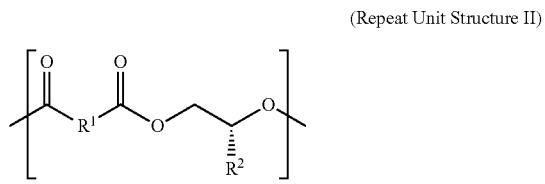

(Repeat Unit Structure II)

or ii) individual repeat units having both Repeat Unit Structure I and Repeat Unit Structure II, and wherein $R^1$ is selected from —$(CH_2)_x$—, where x is 2-6, cis or trans —$CR^3$=$CR^4$—, where $R^3$ and $R^4$ are selected from —H, —CH$_3$, and —Cl, —CH$_2$C(=CH$_2$)—, ortho —C$_6$H$_4$—, —CH$_2$OCH$_2$—, 1,8-naphthylenediyl, and 3,4-cyclohexenediyl, R$^2$ is selected from —CH$_3$, —CF$_3$, C$_2$ to C$_8$ alkyl group or aryl group, —CH$_2$OR$^5$, where R$^5$ is a C$_2$ to C$_8$ alkyl group or aryl group, and —CH$_2$X, where X is Cl, Br, I, or F. In an embodiment, 95% or greater of the stereocenters in the individual repeat units of the first enantiomeric polymer chains have Repeat Unit Structure I, 95% or greater of the stereocenters in the individual repeat units of the second enantiomeric polymer chains have Repeat Unit Structure II, the ratio of first enantiomeric polymer chains to second enantiomeric polymer is 1:19 to 19:1, the first enantiomeric polymer chains comprise 20 to 5000 individual repeat units of the Repeat Unit Structure I, and the second enantiomeric polymer chains comprise 20 to 5000 individual repeat units of the Repeat Unit Structure II. In an embodiment, the ratio of first enantiomeric polymer chains to second enantiomeric polymer chains ranges from 1:9 to 9:1.

In an embodiment, the first enantiomeric polymer chain and/or second enantiomeric polymer chain further comprises a small molecule and/or polymer chain covalently bound to the first enantiomeric polymer chain and/or second enantiomeric polymer chain. In an embodiment, one or more of the first enantiomeric polymer chains has the following structure:

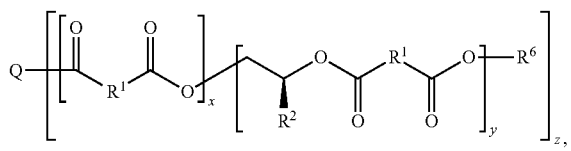

where x is 0 or 1, y is 10 to 5000, and z is 1 to 100, and/or one or more of the second enantiomeric polymer chains has the following structure:

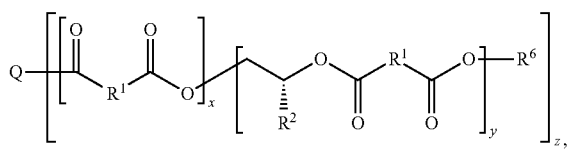

where x is 0 or 1, y is 10 to 5000, and z is 1 to 100, R$^6$ is a C$_2$ to C$_8$ hydroxyalkyl group or hydrogen atom, and Q is a polymeric chain or a small molecule and is attached to the enantiomeric polymer chain by an ester linkage.

In an embodiment, the first enantiomeric polymer chains are random copolymers comprising the following structure:

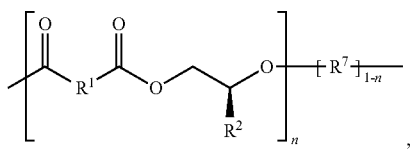

where n is 0.20 to 0.99, and the second enantiomeric polymer chains are random copolymers comprising the following structure:

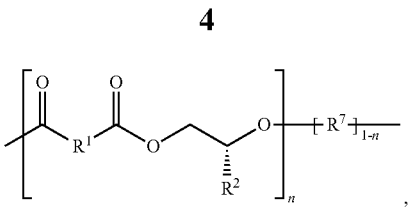

wherein n 0.20 to 0.99, the ratio of first enantiomeric polymer chains to second enantiomeric polymer chains is 1:19 to 19:1, and R$^7$ is —CO$_2$R$^8$O—, where R$^8$ is selected from C$_2$ to C$_8$ alkyl linker group or aryl linker group, —CO(CH$_2$)$_x$O—, where x is 2-5, —COCHR$^9$O—, where R$^9$ is a C$_2$ to C$_8$ alkyl group or aryl group, or —CH$_2$CHR$^{10}$O—, where R$^{10}$ is —CH$_3$, —CF$_3$, C$_2$ to C$_8$ alkyl group or aryl group, —CH$_2$OR$^{11}$, where R$^{11}$ is a C$_2$ to C$_8$ alkyl group or aryl group, and —CH$_2$X, where X is Cl, Br, I, or F. In an embodiment, the ratio of first enantiomeric polymer chains to second enantiomeric polymer chains is 1:9 to 9:1.

In an embodiment, the first enantiomeric polymer chains are random copolymers comprising the following structure:

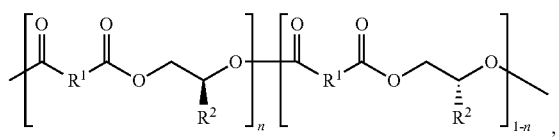

where n is 0.60 to 0.99 and the individual n repeat units have a first configuration and the individual 1-n repeat units has a second configuration that is the opposite absolute stereochemistry of the first configuration, the second enantiomeric polymer chains are random copolymers comprising the following structure:

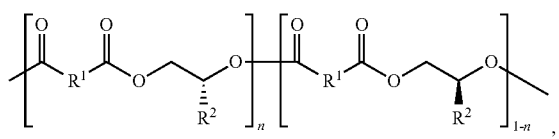

where n is 0.60 to 0.99 of the composition and the individual n repeat units have a first configuration and the individual 1-n repeat units have a second configuration that is the opposite absolute stereochemistry of the first configuration, and the ratio of first enantiomeric polymer chains to second enantiomeric polymer chains is 1:19 to 19:1. In an embodiment, the ratio of first enantiomeric polymer chains to second enantiomeric polymer chains is 1:9 to 9:1.

In an embodiment, wherein the enantiomeric polymer chains are stereoblock copolymers of the following structure:

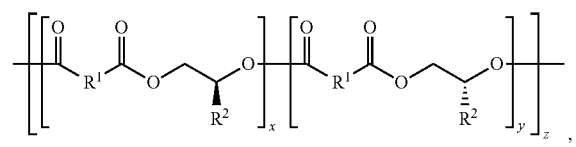

where x is 10 to 1000 and y is 10 to 1000 and z is 1 to 100, the ratio of x and y is 1:19 to 19:1.

In an embodiment, an article of manufacture comprises a composition of the present disclosure. In various embodiments, the article of manufacture is a packaging material, disposable tableware, an agricultural film, loose-fill packaging, a compost bag, upholstery, or a disposable garment. In various other embodiments, the article of manufacture is a biomedical device, a drug delivery device, an awning, a feminine hygiene product, a diaper, or a component thereof.

DETAILED DESCRIPTION OF THE DISCLOSURE

Figure 1:
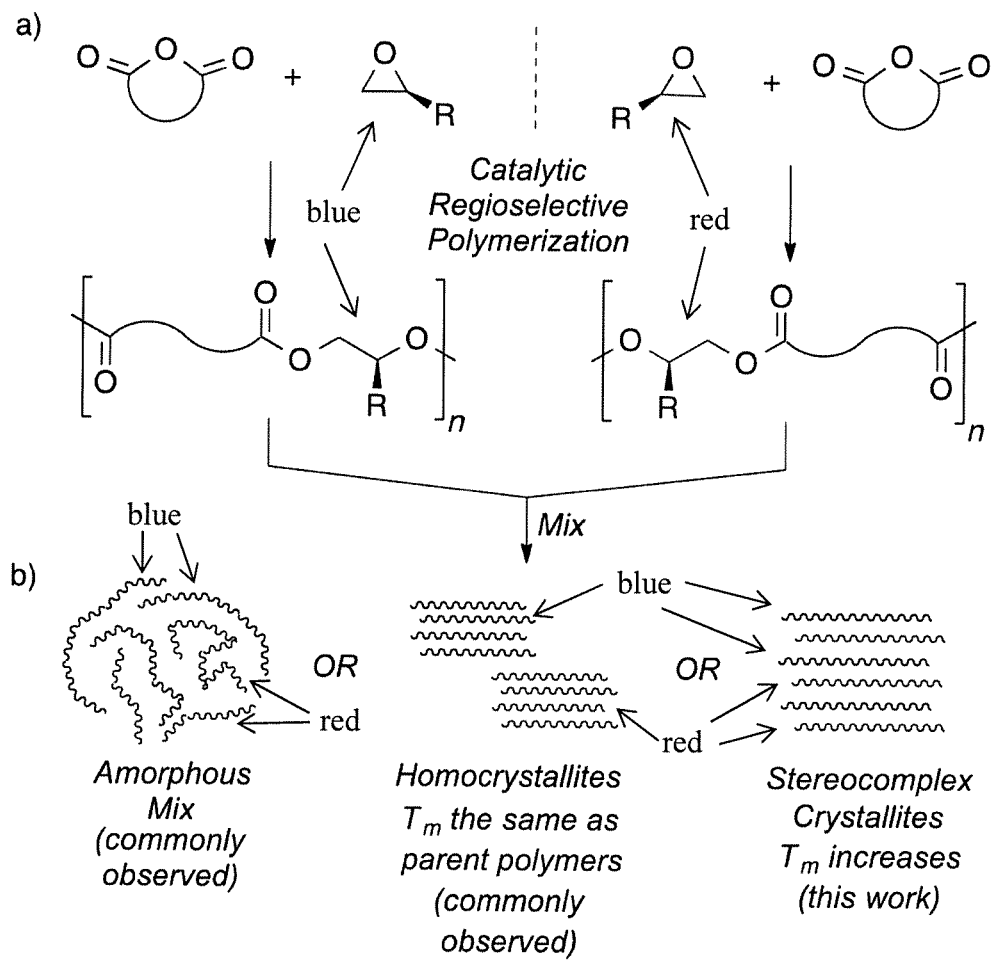
FIG. 1. a) Example of regioselective polymerization of cyclic anhydrides and epoxides b) crystallization of the mixed polymer chains.

As used herein, unless otherwise expressly stated, "alkyl group" or "alkyl linker group" refers to branched or unbranched saturated hydrocarbon groups. Examples of an alkyl group include methyl group, ethyl group, n-propyl group, i-propyl group, n-butyl group, i-butyl group, s-butyl group, pentyl group, hexyl group, heptyl group, and octyl group. The alkyl group can be unsubstituted or substituted. The alkyl group can be a terminal group and the alkyl linker group can be covalently bound to two other groups. Example of substituent groups include halides (—F, —Cl, —Br, and —I), alkoxides, carboxylates, carboxylic acids, and ether groups. Alkyl group also includes the alkyl moiety of a hydroxyalkyl group.

As used herein, unless otherwise expressly stated, "aryl group" or "aryl linking group" refers to anaromatic cyclic compound having a ring in which all of the atoms forming the ring are carbon atoms or an aromatic cyclic compound having a ring in which all of the atoms forming the ring are carbon atoms and one or more heteroatoms (e.g., nitrogen atoms and/or sulfur atoms). The aryl group is any functional group derived from an aromatic ring. The aryl groups or aryl linking group can be a terminal group or be covalently bound to two other groups. Examples of aryl groups include phenyl, tolyl, xylyl, naphthyl, thienyl, pyridyl rings (i.e., groups), and substituted analogs thereof. The aryl group can be substituted with groups such as halides and/or alkyl chains in the ortho position, meta position, para position, or a combination thereof. The aryl group can be unsubstituted or substituted. Examples of substituent groups include alkyl groups, halides (—F, —Cl, —Br, —I), alkoxides, carboxylates, carboxylic acids, and ether groups.

The present disclosure provides compositions comprised of stereocomplexes of enantiomeric polymer chains have repeat units formed from a ring-opening reaction of an epoxide (e.g., an enantiopure epoxide) followed by a ring-opening of a cyclic anhydride (e.g., the enantiomeric polymer chains comprise repeat units formed from a ring-opening reaction of an enantiopure epoxide followed by a ring-opening of a cyclic anhydride). Also provided are methods of making the compositions and uses of the compositions.

The disclosure is based at least in part on the surprising and unexpected discovery that (S)- and (R)-poly(propylene succinate), which individually crystallize very slowly and at low temperatures, can be combined to form a material that crystallizes three orders of magnitude faster and that melts at a temperature up to 40° C. higher than the parent polymers alone. While there are some other examples of polymer stereocomplexes, this is the first example of a polyester stereocomplex synthesized from epoxides and cyclic anhydrides. In addition, this polyester stereocomplex is formed from very inexpensive and readily accessible starting materials and is expected to be biodegradable, and the byproducts formed by the degradation of the stereocomplex are non-toxic succinic acid and propylene glycol.

Disclosed is, for example, formation of a stereocomplex from racemic, isotactic, regioregular chains of poly(propylene succinate) synthesized via ring-opening alternating copolymerization that demonstrates improved thermal properties and crystallinity in comparison to the enantiopure parent polymers. The stereocomplexation is a route to a new class of semicrystalline polyesters with improved properties, produced from inexpensive, readily accessible starting materials.

In an aspect, the present disclosure provides compositions. The compositions comprise enantiomeric polymer chains that form one or more stereocomplexes.

The enantiomeric chains have repeat units formed from a ring-opening reaction of an epoxide (e.g., an enantiopure epoxide) followed by a ring-opening of a cyclic anhydride (e.g., the enantiomeric polymer chains comprise repeat units formed from a ring-opening reaction of an enantiopure epoxide followed by a ring-opening of a cyclic anhydride). The enantiomeric chains may have the same or opposite absolute stereochemistry. For example, the compositions comprise two types of enantiomeric polymer chains and each type enantiomeric polymer chains comprise repeat units of a single absolute stereochemistry. In another example, the compositions comprise enantiomeric polymer chains that comprise two types of repeat units (i.e., repeat units of complementary (i.e., opposite) absolute stereochemistry).

For example, the enantiomeric polymer chains i) comprise both first enantiomeric polymer chains having a first enantiomeric structure and comprise individual repeat units having the following structure:

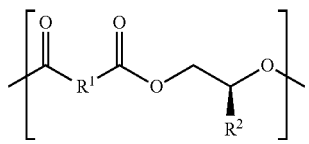

(Repeat Unit Structure I)

and second enantiomeric polymer chains having a second enantiomeric structure that is the opposite absolute stereochemistry of the first enantiomeric structure and comprise individual repeat units having the following structure:

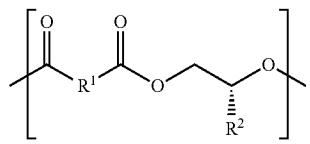

(Repeat Unit Structure II)

or ii) comprise individual repeat units having both Repeat Unit Structure I and Repeat Unit Structure II. $R^1$ is selected from —$(CH_2)_x$— (x is 2-6) and cis or trans —$CR^3$=$CR^4$—, where $R^3$ and $R^4$ are selected from —H, —$CH_3$, and —Cl, —$CH_2C(=CH_2)$—, ortho —$C_6H_4$—, —$CH_2OCH_2$—, 1,8-naphthylenediyl, and 3,4-cyclohexene-diyl. $R^2$ is a —$CH_3$, —$CF_3$, $C_2$ to $C_8$ alkyl group or aryl group, —$CH_2OR^5$, where $R^5$ is a $C_2$ to $C_8$ alkyl group or aryl group, or —$CH_2X$ (X is Cl, Br, I, or F). All of the R groups (e.g., $R^1$ and $R^2$ groups) may be the same in the first and second enantiomeric chains. In various embodiments, 80% or greater, 90% or greater, 95% or greater, 96%, 97%, 98%, or 99% of the R groups (e.g., $R^1$ and $R^2$ groups) are the same in the first and second enantiomeric chains.

In various embodiments, 50% or greater, 60% or greater, 70% or greater, 80% or greater, 90% or greater, 95% or greater, 99% or greater, or all of the stereocenters in the individual repeat units of the first enantiomeric polymer chains have Repeat Unit Structure I and/or 50% or greater, 60% or greater, 70% or greater, 80% or greater, 90% or greater, 95% or greater, 99% or greater, or all of the stereocenters in the individual repeat units of the second enantiomeric polymer chains have Repeat Unit Structure II. The first enantiomeric polymer chains comprise 20 to 5000 individual repeat units of Repeat Unit Structure I, including all integer number of individual repeat units and ranges therebetween. The second enantiomeric polymer chains comprise 20 to 5000 individual repeat units of Repeat Unit Structure II, including all integer number of individual repeat units and ranges therebetween.

The amount of enantiomeric polymer chains in the composition can vary. For example, the composition can comprise from 0.1 weight % to 99.9 weight %, including all 0.1 weight % values and ranges therebetween, of the enantiomeric polymer chains. In an embodiment, the composition consists of the enantiomeric polymer chains. In an embodiment, the composition consists essentially of the enantiomeric polymer chains.

Where the composition comprises two or more types of enantiomeric polymer chains, the ratio of the enantiomeric polymeric chains (e.g., first enantiomeric polymer chains and second enantiomeric polymer chains) can vary. For example, the composition comprises 5 mol % to 95 mol %, including all integer mol % values and ranges therebetween, of one type of enantiomeric chain (e.g., either first or second enantiomeric chains) and 95 mol % to 5 mol % of the other type of enantiomeric chain (e.g., either first or second enantiomeric, where the other enantiomeric chain has the opposite absolute stereochemistry of the one type of enantiomeric chain.

One or more of the enantiomeric chains (e.g., one or more first enantiomeric polymer chains and/or one or more second polymer chains) may further comprise one or more small molecules and/or one or more polymeric chains. The small molecule(s) and/or polymer chain(s) is/are covalently bound to an individual enantiomeric chain (e.g., a first enantiomeric polymer chain and/or second polymer chain). For example, the small molecule and/or polymeric chain is covalently bound to an individual enantiomeric polymer chain and/or second polymeric chain via an ether or ester linkage. It is desirable that the small molecules and polymeric chains have one or more hydroxyl groups (e.g., —OH groups or —C(O)OH groups). Examples of small molecules include molecules that contain one or more hydroxyl groups, such as alkyl diols, glycerol and benzyl alcohols. Examples of polymeric chains include polyvinyl alcohol or other hydroxyl containing polymers, and polyacrylic acid or other carboxylic acid containing polymers.

In an embodiment, one or more of the first enantiomeric polymer chains has the following structure:

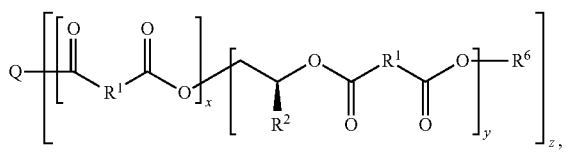

where x is 0 or 1, y is 10 to 5000, including all integer values and ranges therebetween, and z is 1 to 100, including all integer values and ranges therebetween, and/or one or more of the second enantiomeric polymer chains has the following structure:

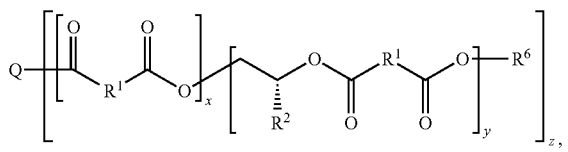

where x is 0 or 1, y is 10 to 5000, including all integer values and ranges therebetween, and z is 1 to 100, including all integer values and ranges therebetween. $R^6$ is a $C_2$ to $C_8$ hydroxyalkyl group or hydrogen atom. Q is a polymeric chain or a small molecule and is attached to the enantiomeric polymer chain by an ester linkage.

One or more of the enantiomeric chains (e.g., one or more first enantiomeric polymer chains and/or one or more second polymer chains) may be a random copolymer. The enantiomeric chain(s) include one or more additional repeat units (in addition to Repeat Unit Structures I and/or II).

For example, the additional repeat unit is —$CO_2R^8O$—, where $R^8$ is $C_2$ to $C_8$ alkyl group or aryl group, —$CO(CH_2)_xO$— (x is 2-5), —$COCHR^9O$—, where $R^9$ is a $C_2$ to $C_8$ alkyl group or aryl group, —$CH_2CHR^{10}O$—, where $R^{10}$ is —$CH_3$, —$CF_3$, $C_2$ to $C_8$ alkyl group or aryl group, or —$CH_2OR^{11}$, where $R^{11}$ is a $C_2$ to $C_8$ alkyl group or aryl group, or —$CH_2X$, where X is Cl, Br, I, or F.

In an embodiment, the first enantiomeric polymer chains are random copolymers comprising the following structure:

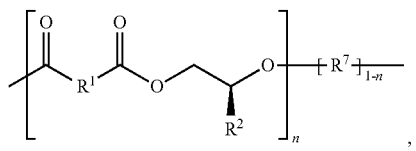

where n is 0.20 to 0.99, including all values to 0.01 and ranges therebetween, and the second enantiomeric polymer chains are random copolymers comprising the following structure:

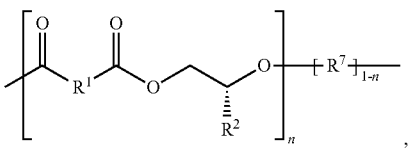

where n 0.20 to 0.99, including all values to 0.01 and ranges therebetween. $R^7$ is —$CO_2R^8O$—, wherein $R^8$ is $C_2$ to $C_8$ alkyl group or aryl group, —$CO(CH_2)_xO$— (x is 2-5), —$COCHR^9O$—, where $R^9$ is a $C_2$ to $C_8$ alkyl group or aryl group, —$CH_2CHR^{10}O$—, where $R^{10}$ is —$CH_3$, —$CF_3$, $C_2$ to $C_8$ alkyl group or aryl group, or —$CH_2OR^{11}$, where $R^{11}$ is a $C_2$ to $C_8$ alkyl group or aryl group, or —$CH_2X$, where X is Cl, Br, I, or F. In this embodiment, the ratio of first enantiomeric polymer chains to second enantiomeric polymer chains is, for example, 1:19 to 19:1.

In another embodiment, the first polymer chains are random copolymers comprising the following structure:

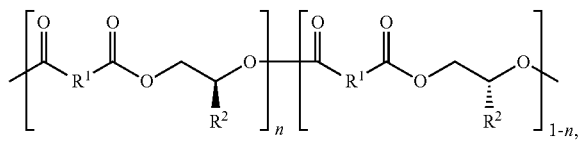

where n is 0.60 to 0.99, including all values to 0.01 and ranges therebetween, and the individual n repeat units have a first configuration and the individual 1-n repeat units have a second configuration that is the opposite absolute stereochemistry of the first configuration. The second polymer chains are random copolymers comprising the following structure:

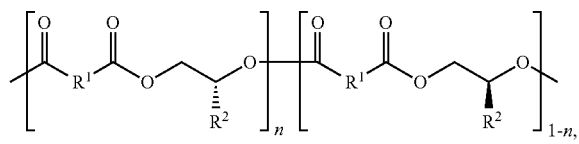

where n is 0.60 to 0.99, including all values to 0.01 and ranges therebetween, and the individual n repeat units have a first configuration and the individual 1-n repeat units have a second configuration that is the opposite absolute stereochemistry of the first configuration. In an embodiment, the ratio of first enantiomeric polymer chains to second enantiomeric polymer chains is, for example, 1:19 to 19:1. In another embodiment, the ratio of first enantiomeric polymer chains to second enantiomeric polymer chains is 1:9 to 9:1.

The composition may comprise enantiomeric polymer chains comprising blocks of individual repeat units having opposite absolute stereochemistry. The enantiomeric polymer chains are stereoblock copolymers. One or more blocks having opposite absolute stereochemistry are adjacent to each other. For example, the individual blocks have 10 to 5000 repeat units, including all integer values and ranges therebetween. For example, the individual enantiomeric polymer chains comprise one or more blocks of Repeat Unit Structure I and one or more blocks of Repeat Unit Structure II.

In an embodiment, the enantiomeric polymer chains are stereoblock copolymers of the following structure:

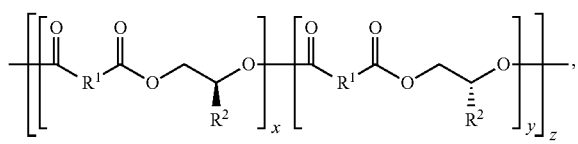

where x is 10 to 1000, including all integer values and ranges therebetween, y is 10 to 1000, including all integer values and ranges therebetween, and z is 1 to 100, including all integer values and ranges therebetween. The ratio of x and y is 1:19 to 19:1, including all integer ratio values therebetween.

The individual enantiomeric polymer chains have end groups. For example, the end groups are H, OH, $CO_2H$, Cl, Br, I, F, or $NO_3$.

The individual enantiomeric polymer chains have a variety of molecular weights. For example, the enantiomeric polymer chains have a number average molecular weight of 1 to 100 kDa, including all integer kDa values and ranges therebetween. Methods of determining the molecular weight are known in the art. For example, the number average ($M_w$) of the enantiomeric polymer chains is determined by comparison with polystyrene standards or by light scattering methods.

The enantiomeric polymer chains have a variety of polydispersity. For example, the individual enantiomeric polymer chains have a polydispersity of 1.00 to 5.99. Methods of determining the molecular weight are known in the art. For example, the polydisperisty of the enantiomeric polymer chains is determined by comparison with polystyrene standards or by light scattering methods.

The compositions comprise one or more stereocomplexes in a crystalline form. The stereocomplexes are formed by interaction of two enantiomeric polymer chains having opposite absolute stereochemistry (e.g., stereoregular complementary polymers).

The stereocomplexes provide a polymeric material with desirable properties. The desirable properties include increased melting transition ($T_m$) and crystallinity. For example, the polymeric material exhibits an increased $T_m$ at least 20° C., and up to 40° C. higher than the $T_m$ of the individual enantiomeric polymer chains having the same absolute stereochemistry. In addition, the stereocomplexes crystallize up to 1000 times faster than the individual enantiomeric polymer chains. There is no crystallinity in the individual enantiomeric polymers directly from the melt, while the stereocomplexes have 50-60% crystallinity from the melt.

The composition may comprise other materials. Examples of other materials include other polymer materials, fillers, colorants, stabilizers, plasticizers, crosslinkers, reinforcers. The other materials can be organic materials or inorganic materials.

The composition can be in a variety of forms. For example, the composition is in solid form (e.g., sheets, pellets, rods, or powder).

In an aspect, the present disclosure provides methods of making compositions of the present disclosure. A variety of methods of making the compositions can be used.

The compositions can be made by mixing desired amounts of two or more types of enantiomeric polymer chains, where the two types of enantiomeric polymer chains have the opposite absolute stereochemistry. Accordingly, in an embodiment, a method of making a composition comprising enantiomeric polymer chains that form one or more stereocomplexes comprises mixing desired amounts of two or more types of enantiomeric polymer chains, where the two types of enantiomeric polymer chains have the opposite absolute stereochemistry.

Individual enantiomeric polymer chains having the same absolute stereochemistry can be made by methods known in the art. For example, an enantiopure epoxide is reacted with a cyclic anhydride in the presence of a catalyst and co-catalyst. Examples of synthesis of enantiomeric polymer chains are described herein.

The enantiopure epoxide may be reacted with the cyclic anhydride in the presence of a small molecule or other monomers to provide copolymers comprising individual polyester repeat units.

A mixture of individual enantiomeric polymer chains having opposite absolute stereochemistry can be made in situ by reacting a racemic mixture of an epoxide with a cyclic anhydride. Accordingly, in an embodiment, a method of making a composition comprising enantiomeric polymer chains that form one or more stereocomplexes comprises reacting a racemic mixture of an epoxide with a cyclic anhydride in the presence of a catalyst to form enantiomeric polymer chains that crystallize in situ to form one or more stereocomplexes.

The enantiomeric polymeric chains can be modified after synthesis. Methods of such modification are known in the art.

In an aspect, the present disclosure provides uses of the compositions of the present disclosure. The compositions can be used in a variety of applications. For example, the compositions can be used as substitutes for materials such as low density polyethylene.

The compositions can be used in biomedical and drug delivery applications. For example, the compositions can be used in orthopedics, facial fracture repair, tissue engineering, ureteral and cardiac stents, as antimicrobial or antitumor agents, as drug carriers, or as medical implants in the form of anchors, screws, plates, pins, rods, and as a mesh.

In an embodiment, an article of manufacture comprises a composition of present disclosure. Examples of article of manufactures include packaging materials (e.g., for foods or other devices), disposable tableware, biomedical devices (or a component thereof), drug delivery devices (or a component thereof), agricultural films, loose-fill packaging materials, compost bags (or a component thereof), upholstery, disposable garments (or a component thereof), awnings (or a component thereof), feminine hygiene products (or a component thereof), and diapers (or a component thereof).

The following examples are presented to illustrate the present disclosure. They are not intended to limiting in any manner.

Example 1

The following is an example of the preparation and characterization of a stereocomplex of the present disclosure.

Because of their possible biodegradability and functional diversity, aliphatic polyesters have the potential to be useful in a wide array of commercial applications. However, for polyesters to compete industrially with the most widely used polyolefins, they should be comparable in performance. The ring-opening alternating copolymerization of cyclic anhydrides and epoxides combines wide substrate scope with the potential for control of microstructure afforded by chain-growth polymerization. Herein we show the formation of a stereocomplex from racemic, isotactic, regioregular chains of poly(propylene succinate) synthesized via this method that demonstrates improved thermal properties and crystallinity in comparison to the enantiopure parent polymers. We demonstrate that stereocomplexation is a route to a new class of semicrystalline polyesters with improved properties, produced from inexpensive, readily accessible starting materials.

Polyesters synthesized via the ring-opening alternating copolymerization (ROAC) of epoxides and cyclic anhydrides can be made by purely chemical means with a wide array of inexpensive starting materials (FIG. 1). This method also provides a large substrate scope and allows for control over polymer microstructure. Additionally, our group has recently discovered that the regioregular ROAC of enantiopure propylene oxide with some cyclic anhydrides results in increased crystallinity of the resulting polyesters. Because these polyesters are also chiral, using enantiopure epoxides results in two enantiomerically pure forms of each polymer. The handedness of the polyesters opens up the possibility of stereocomplexation between polymer chains of R and S configurations. Stereocomplexation, in turn, results in different crystal structures and generally higher melting temperatures, thus increasing the potential for commercialization of polyesters, which often suffer from poor thermal properties and relatively low levels of crystallinity in comparison to polyolefins.

Stereocomplexation occurs when a stereoselective interaction between two stereoregular complementary polymers in the crystalline state results in altered physical and thermal properties in comparison to the parent polymers. Most commonly, stereocomplexes are formed between enantiomerically complementary polymer strands. Stereocomplexation improves and allows for tunability of polymer properties, including crystallinity as well as biodegradability. In this report, we utilize salen cobalt complexes with ionic cocatalysts for the synthesis of regioregular poly (propylene succinate). We screened for stereocomplex formation by regioselectively polymerizing both (R)- and (S)-propylene oxide separately with succinic anhydride and subsequently mixing the resulting polyesters. The properties of the mixed samples were then compared to those of the parent polymers (FIG. 1).

While an amorphous mix or racemic conglomerates of homocrystallites are commonly observed when enantiomerically pure polymers are mixed, we show that this strategy resulted in the formation of a stereocomplex from enantiomeric strands of isotactic poly(propylene succinate), producing a material with an increased $T_m$ and a greater level of crystallinity. Not only is poly(propylene succinate) formed from inexpensive monomers and likely to be biodegradable, the stereocomplex exhibits a $T_m$ comparable to low density PE. In addition, succinic anhydride (SA) is an attractive cyclic anhydride monomer because its synthesis from biorenewable resources has expanded widely in recent years.

Figure 2:
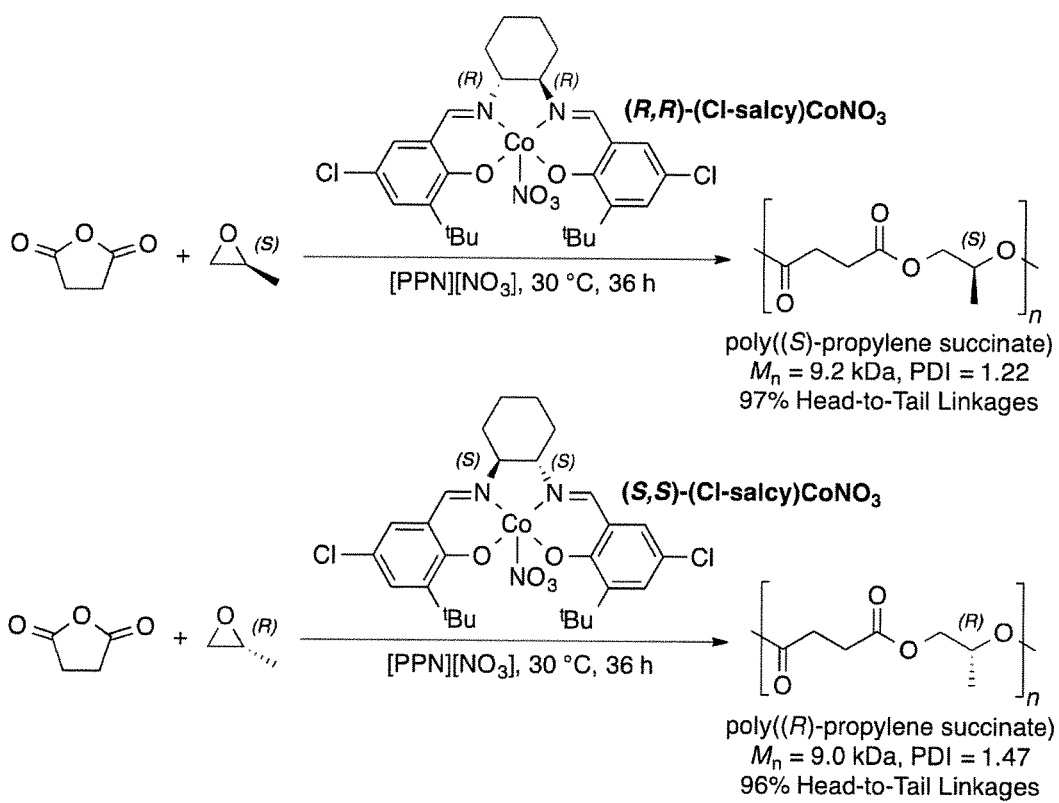
FIG. 2. Example of regioselective alternating copolymerization of enantiopure propylene oxide and succinic anhydride.

To form the polyester stereocomplex we first synthesized poly(S)- and poly((R)-propylene succinate) from (S)- and (R)-propylene oxide (PO), respectively (FIG. 2). (salcy) CoNO$_3$ (salcy=N,N'-bis(salicylidene)cyclohexanediamine) complexes with bis(triphenylphosphine)iminium nitrate ([PPN][NO$_3$]) were previously used as cocatalysts for the regioselective ROAC of various cyclic anhydrides and epoxides. Poly(propylene succinate) regioregularity was analyzed by gas chromatography of methyl diester derivatives of the diol products that resulted from degrading the enantiopure samples under basic conditions. High regioregularity (97% head-to-tail linkages) was observed when a chloro group was present in the para position of the salicylidene moiety of the catalyst, (Cl-salcy)CoNO$_3$. In addition, regioregularity was optimized when each enantiomer of the epoxide was polymerized with the opposite enantiomer of catalyst. Copolymerization of (S)—PO with SA proceeded to full conversion in 36 hours at 30° C. using enantiopure (R,R)—(Cl-salcy)CoNO$_3$ to give polymer with an $M_n$ of 9.2 kDa and a PDI of 1.22. Likewise, polymerization of (R)—PO proceeded using (S,S)—(Cl-salcy)CoNO$_3$ to give polymer with an $M_n$ of 9.0 kDa and a PDI of 1.47.

Figure 3:
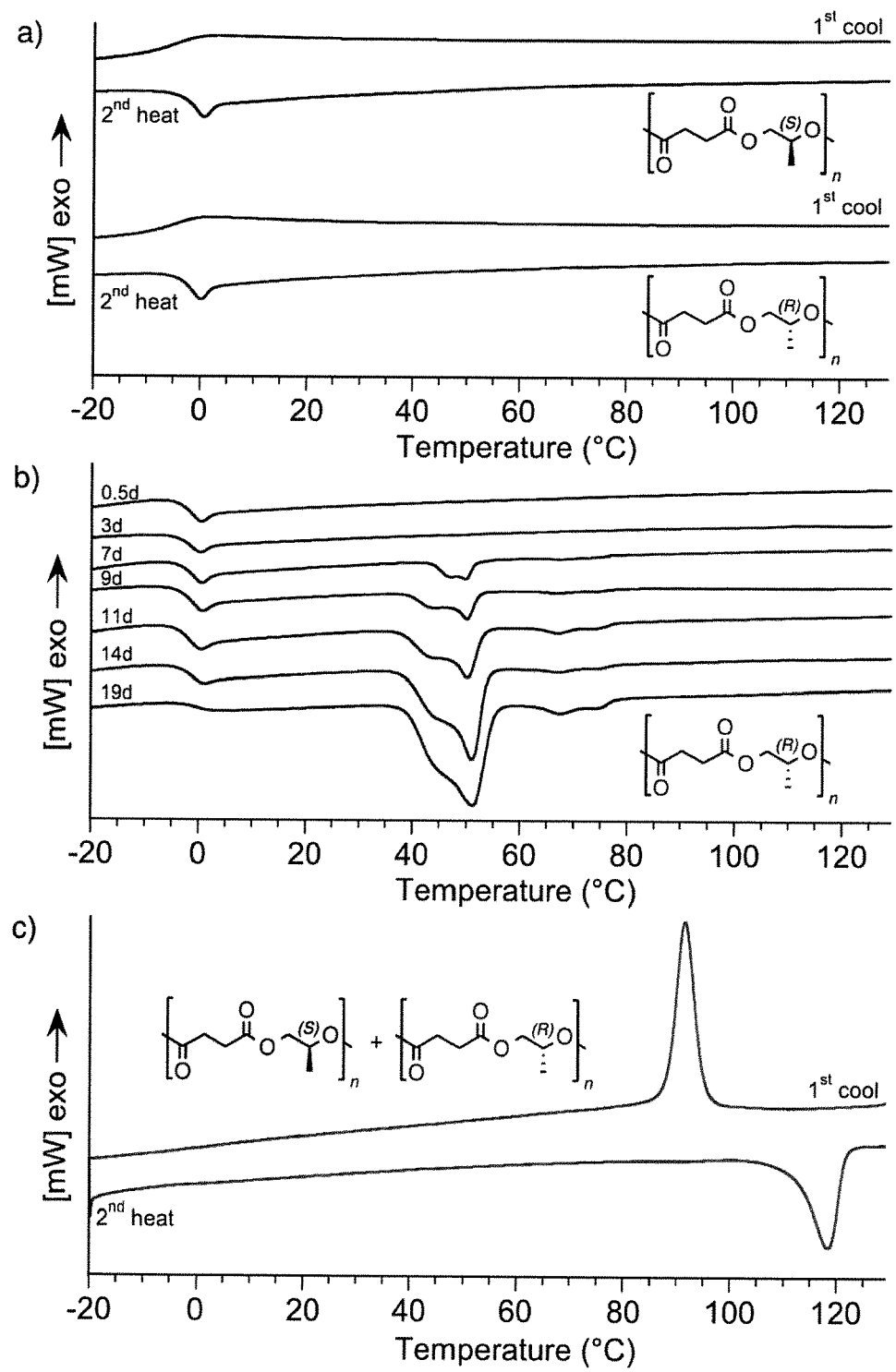
FIG. 3. DSC traces of a) isotactic poly((S)-propylene succinate) and poly((R)-propylene succinate) from the melt, b) crystallization of poly((R)-propylene succinate over time, and c) the stereocomplexed mixture of both polymers.

Differential scanning calorimetry (DSC) was used to investigate the thermal properties of the enantiopure, regioregular polymers and of the mixed specimens. The thermograms of both poly((R)-propylene succinate) and poly((S)-propylene succinate) show no crystallinity, and only a glass transition ($T_g$) of –4° C. is observed (FIG. 3a). FIG. 3b shows that the parent polymers do slowly crystallize from the melt, with crystallinity first appearing after about one week and gradually increasing over time. For poly((R)-propylene succinate) after 19 days, a relatively large amount of a low melting polymorph ($T_m$ around 50° C.) is observed, along with a very small amount of a higher melting polymorph ($T_m$ around 70° C.). Some degree of crystallinity is observed from precipitation of the enantiopure polymers with methanol, and a $T_m$ of 79° C. can be obtained, although this method is not ideal for industrial applications as the resulting polymer is a fine powder and crystallinity disappears completely upon melting and no $T_m$ is seen on the second heat.

To test for stereocomplex formation, dissolved solutions of poly((S)-propylene succinate) and poly((R)-propylene succinate) in dichloromethane were mixed and the solvent was allowed to evaporate slowly. The sample was then dissolved again in dichloromethane and precipitated by adding methanol dropwise with vigorous stirring. DSC was performed on the sample after drying under reduced pressure, and the thermal properties of the poly(propylene succinate) stereocomplex in comparison to the enantiomeric polymers can be seen in FIG. 3c. In the stereocomplex, not only does the melting point increase by approximately 40° C. to 120° C. on the first heat relative to the enantiopure polymers, recrystallization around 92° C. occurs upon cooling and the same $T_m$ is observed on the second heat.

It was discovered that both the rate of heating and cooling and the maximum temperature of heating affected the recrystallization of the stereocomplex but had no effect on the enantiopure polymers. All polymers shown in FIG. 3 were heated to a maximum temperature of 130° C., but while the enantiopure polymers in FIGS. 3a and 3b were heated at a rate of 10° C./min, the stereocomplex was heated at 2° C./min to optimize the recrystallization temperature.

The immediate recrystallization of the stereocomplex upon cooling shows a vast improvement over any other polyester formed from the ROAC of propylene oxide and a cyclic anhydride reported to date. While there are examples of semicrystalline polyesters formed with this method, all of them show crystallinity only from solution and not from the melt after initial heating above the $T_m$. The $T_{1/2}$ of was calculated for both the parent polymers and the stereocomplex, and was found to be approximately three orders of magnitude greater for the parent polymers than for the stereocomplex.

Figure 4:
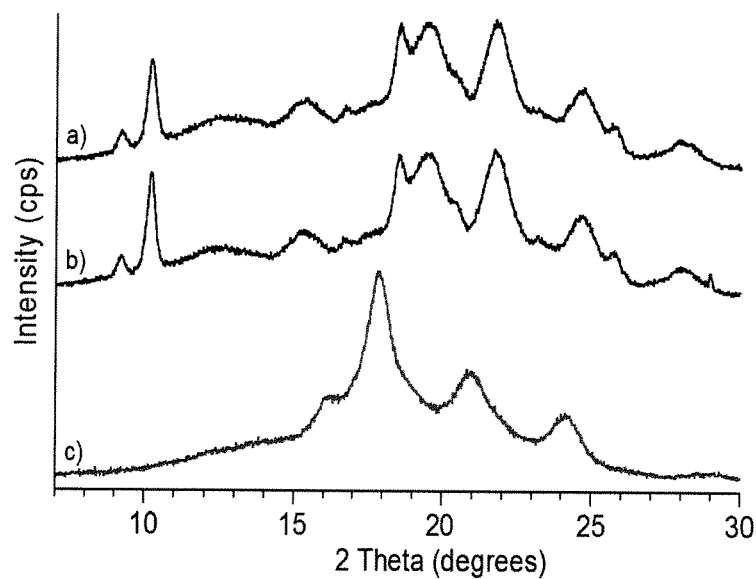
FIG. 4. Powder XRD profiles of a) (S)-poly(propylene succinate), b) (R)-poly(propylene succinate), and c) stereocomplexed poly(propylene succinate).

Powder X-ray diffraction (XRD) was used to confirm the formation of a stereocomplex via the presence of different crystalline diffraction peaks in comparison to the parent polymers. Samples for both the enantiomerically pure, isotactic polymers and the stereocomplex were prepared by crystallization via dropwise addition of methanol to a dichloromethane solution of the polymer or polymer mixture in order to induce crystallization, especially in the case of the parent polymers. FIG. 4 shows the powder XRD profiles of both enantiopure forms of poly(propylene succinate) and of the poly(propylene succinate) stereocomplex. Both poly ((S)-propylene succinate) and poly((R)-propylene succinate) show five large crystalline diffraction peaks, at 10.2°, 18.5°, 19.4°, 21.8°, and 24.7°, along with four smaller peaks at 9.2°, 15.4°, 16.8°, and 25.7°. In contrast, the polymer stereocomplex shows three large peaks at 17.9°, 20.8°, and 24.1° that are not present in the enantiopure polymer samples. Additionally, the stereocomplex shows one small peak at 16.2°.

Figure 5:
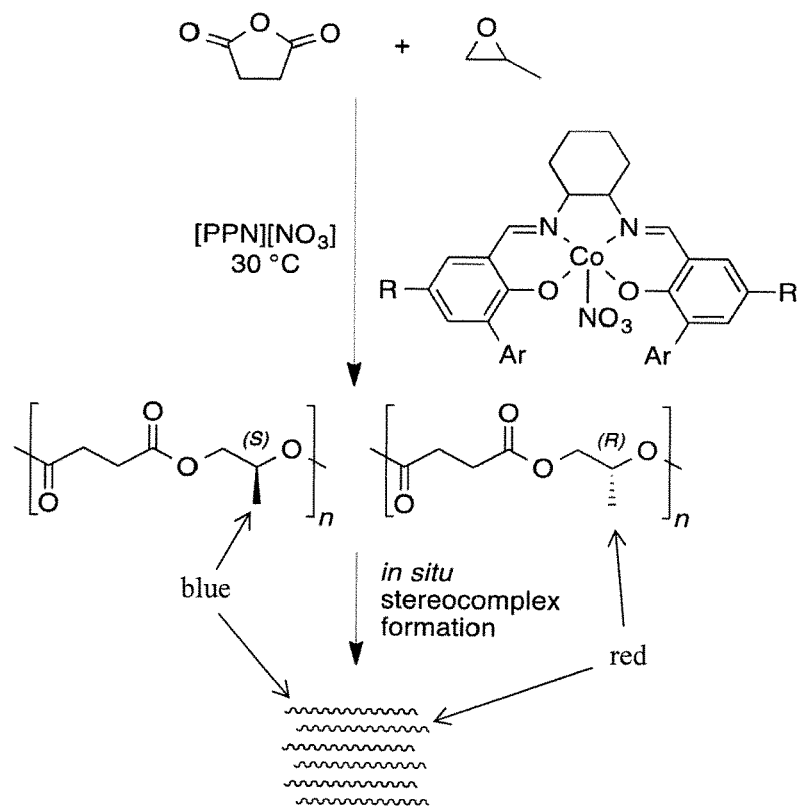
FIG. 5. Copolymerization of racemic propylene oxide with racemic (salcy)Cobalt catalysts for in situ stereocomplex formation.
Figure 6:
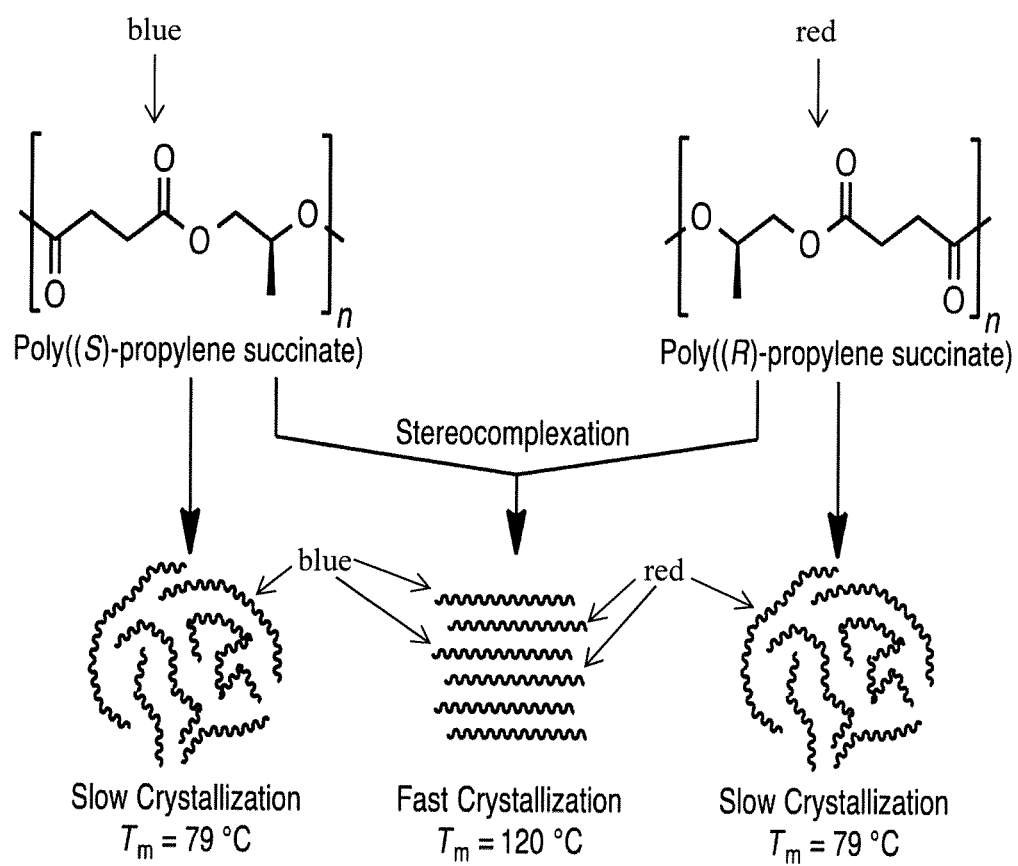
FIG. 6. An example of a stereocomplex of the present disclosure.

Isoselective polymerization of racemic epoxides is expected to provide in situ stereocomplex formation eliminating the need for enantiopure starting materials (FIG. 5). Salcy-type catalysts with various aryl groups present in the ortho positions and various R groups in the para positions have been shown to be capable of stereoselectively polymerizing racemic propylene oxide with succinic anhydride, as well as other terminal and disubstituted epoxides and cyclic anhydrides.

We discovered the formation of a new polymer stereocomplex from enantiomeric poly(propylene succinate) with significantly improved thermal properties and increased crystallinity compared to the enantiopure parent polymers. By optimization of the ring-opening alternating copolymerization of succinic anhydride with enantiopure propylene oxide and subsequent stereocomplex formation, a new class of semicrystalline biodegradable polyesters has been established. In addition, we have shown that a relatively high $T_m$ semicrystalline material with a $T_m$ similar to low density PE can be created from two very slow-crystallizing, low $T_m$ aliphatic polyesters. Various terminal epoxides and disubstituted epoxides can be combined with the wide scope of available cyclic anhydrides via the alternating copolymerization described above, and combination of any number of these racemic isotactic polymers is expected to produce new polymer stereocomplexes.

General Considerations. All manipulations of air and water sensitive compounds were carried out under dry nitrogen using a Braun Labmaster Glovebox or standard Schlenk line techniques. $^1$H and $^{13}$C NMR spectra were recorded on a Varian INOVA 400 ($^1$H, 400 MHz), or Varian INOVA 500 ($^1$H, 500 MHz) spectrometer. $^1$H NMR spectra were referenced with residual non-deuterated solvent shifts (CHCl$_3$=7.26 ppm) and $^{13}$C NMR spectra were referenced by solvent shifts (CDCl$_3$=77.16 ppm).

Gel permeation chromatography (GPC) analyses were carried out using an Agilent PL-GPC 50 integrated system (2×PLgel Mini-MIX C columns, 5 micron, 4.6 mmID) equipped with UV and refractive index detectors. The GPC columns were eluted at a rate of 0.3 mL/min with tetrahydrofuran (30° C.) and were calibrated relative to monodisperse polystyrene standards.

Differential scanning calorimetry of polymer samples was performed on a Mettler-Toledo Polymer DSC instrument equipped with a Julabo chiller and autosampler. DSC experiments were prepared in crimped aluminum pans and standard experiments were conducted with a heating rate of 10° C./min from −70° C. to +200° C. or from −20° C. to +130° C. Stereocomplex crystallization experiments were conducted with a heating rate of 2° C./min from −20° C. to +130° C. Data were processed using StarE software.

Gas chromatography was performed using an HP6890 Series GC System. Propylene oxide enantiomers were separated using a Chiraldex α-cyclodextrin trifluoroacetyl column. The separation method comprised holding at 40° C. for 20 minutes, followed by heating at 20° C./min to 150° C., and then holding at 150° C. for 28 minutes. Methyl ester derivatives were separated with a Supelco Chiraldex 225 column. The separation method for this compound comprised holding at 50° C. for 15 minutes, heating from 50° C. to 60° C. at a rate of 10° C./min, holding at 60° C. for 50 minutes, heating from 60° C. to 180° C. at a rate of 10° C./min, and finally holding at 180° C. for 10 minutes.

X-ray diffraction patterns were recorded on a Scintag Powder X-Ray Diffractometer in 2θ medium resolution Brag Brentano geometry employing Cu Kα line focused radiation at 40 kV, 44 mA power and equipped with a Ge crystal detector fitted with a 1.0 mm radiation entrance slit. Samples were mounted on zero background sample holders by dropping powders from a wide-blade spatula and then leveling the sample surface with the back of the spatula. No sample grinding was used prior to analysis unless otherwise noted. Samples were observed using a step scan from 7-30°, integrating at each point for 5 seconds (Omega=1.0°).

Materials. CaH$_2$ pellets (Strem, 90%) were used as received for drying propylene oxide. All solvents were used as received unless otherwise noted. Propylene oxide was purchased from Sigma-Aldrich, dried over CaH$_2$ for 3 days, vacuum transferred to a flame dried thick walled Schlenk adapted flask under inert atmosphere, degassed via 3 freeze-pump-thaw cycles, and stored in the glove box. Succinic anhydride was purchased from Acros Organics (99% purity), recrystallized from CHCl$_3$, dried at 60° C. under reduced pressure, and stored in the glove box. HPLC grade CH$_2$Cl$_2$ for metallation was purchased from Fischer Scientific and filtered through a solvent purification system under inert atmosphere and degassed with N$_2$ for 1 hour. Ethanol for metallation was purchased from Kroptec, stored over 3 Å sieves and degassed with N$_2$ for 1 hour. Metal precursor Co(NO$_3$)$_2$·6H$_2$O (>99% purity) was purchased from Strem and stored in a desiccator until use. Bis(triphenylphosphine) iminium chloride was purchased from Sigma-Aldrich and recrystallized by layering CH$_2$Cl$_2$/Et$_2$O. NMR solvents were purchased from Cambridge Isotopes and stored over 3 Å molecular sieves. All other reagents were purchased from commercial sources and used as received.

Synthesis of Catalyst and Cocatalysts. A N,N'-bis(salicylidene)cyclohexanediimine (salcy)cobalt(III)-type catalyst with a chloro substituent in the para position of the salicylidene moiety was synthesized for the regioregular formation of poly((S)-propylene succinate) and poly((R)-propylene succinate) utilized for stereocomplex formation. A discussion of the regioregularity of poly(propylene succinate) formed from this catalyst can be found below.

Salicylaldehyde Synthesis.

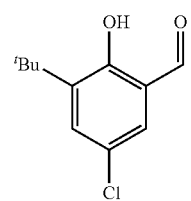 [SMILES: CC(C)(C)c1cc(Cl)cc(C=O)c1O]

The ligand precursor 3-tert-butyl-5-chlorosalicylaldehyde has been previously reported, and $^1$H NMR assignments are included that match well with those in the literature. The yield represents average isolated yields. The precursor to the salicylaldehyde, 2-tert-butyl-4-chlorophenol, was synthesized according to literature procedure. 4-Chlorophenol (Combi-Blocks, 8.00 g, 62.2 mmol) was dissolved in tert-butyl alcohol (Aldrich, 11.9 mL, 124 mmol), and 7.50 mL of concentrated $H_2SO_4$ was added dropwise over 5 minutes, turning the solution from a pale yellow to a light orange. The solution was stirred for 2 days, neutralized with $Na_2CO_3$ (aq), and then extracted into diethyl ether and dried over $Na_2SO_4$. The product was concentrated and purified by column chromatography (95:5, hex:EtOAc) resulting in a yellow oil (71% isolated yield). Using a modified Duff reaction, 2-tert-butyl-4-chlorophenol was formylated as reported by Jacobsen et al. The product was purified by column chromatography (90:10, hex:EtOAc) to yield a crystalline yellow solid (24% isolated yield). $^1H$ NMR spectrum in ppm ($CDCl_3$, 400 MHz): δ 11.72 (s, 1H); 9.82 (s, 1H); 7.46 (d, J=2.6 Hz, 1H); 7.38 (d, J=2.6 Hz, 1H); 1.41 (s, 12H).

N,N'-Bis(3-tert-butyl-5-Cl-salicylidine)-1,2-cyclohexadiimine Synthesis

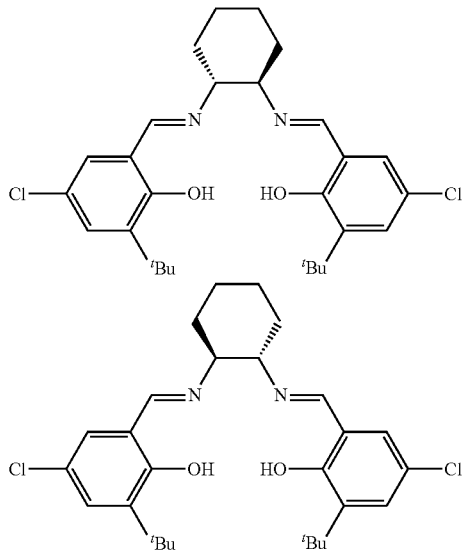

N,N'-Bis(3-tert-butyl-5-Cl-salicylidine)-1,2-cyclohexadiimine has been previously reported, and $^1H$ NMR assignments are included that match well with those in the literature. Yields represent average isolated yields. Both the (R,R) and (S,S) enantiomers of this ligand were prepared. Only preparation of the (R,R)-enantiomer is described, as the only difference between the two is that the opposite enantiomer of tartaric acid is used to prepare the (S,S)-ligand.

(R,R)-1,2-Diaminocyclohexane was prepared according to literature procedure. In a round bottom flask, (L)-(+)-tartaric acid (2.25 g, 15.0 mmol) was added to 7.50 mL deionized $H_2O$. Trans-1,2-diaminocyclohexane (3.60 mL, 30.0 mmol) was added via syringe, followed by 1.50 mL acetic acid, resulting in the formation of a precipitate. The reaction was stirred in an ice bath for 3 hours, and the precipitate collected by filtration, rinsed with cold $H_2O$ and methanol, and dried under reduced pressure to give a white powder.

N,N'-bis(3-tert-butyl-5-chloro-salicylidene)-1,2-cyclohexadiimine was prepared according to literature procedure and the $^1H$ NMR spectrum of the product matched well with the literature. (R,R)-1,2-diaminocyclohexane (0.270 g, 1.02 mmol) and $K_2CO_3$ (0.282 g, 2.04 mmol) were dissolved in 1.36 mL deionized $H_2O$. Ethanol (5.50 mL) was added and the reaction mixture was heated to 80° C. with vigorous stirring. 3-tert-Butyl-5-chlorosalicylaldehyde was dissolved in 3.30 mL ethanol and added slowly to the reaction mixture via syringe. The reaction mixture was then stirred for 2 hours at 80° C. Upon cooling and addition of minimal $H_2O$, the ligand precipitated. The precipitate was collected by filtration and dried under vacuum (80% isolated yield). $^1H$ NMR spectrum ($CDCl_3$, 400 MHz): δ 13.81 (s, 2H); 8.18 (s, 2H); 7.18 (d, J=2.5 Hz, 2H); 6.95 (d, J=2.5 Hz, 2H); 3.31 (m, 2H); 1.99 (bm, 2H); 1.90 (bm, 2H); 1.75 (bm, 2H); 1.48 (bm, 2H); 1.39 (s, 18H).

(Cl-salcy)Cobalt(III)$NO_3$ Complex Synthesis

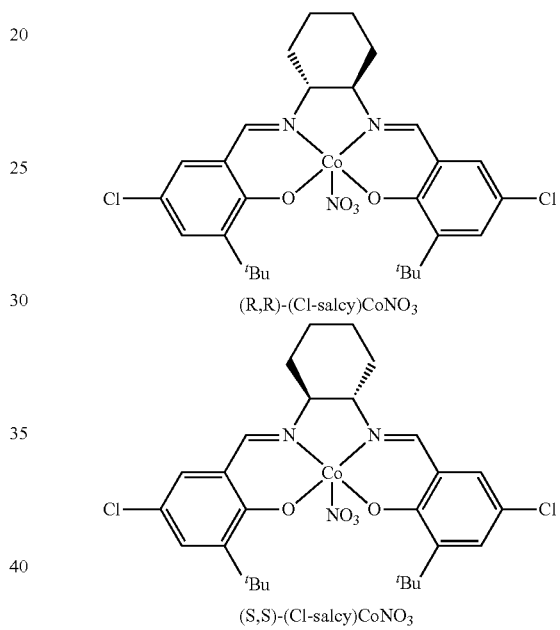

Figure 7:
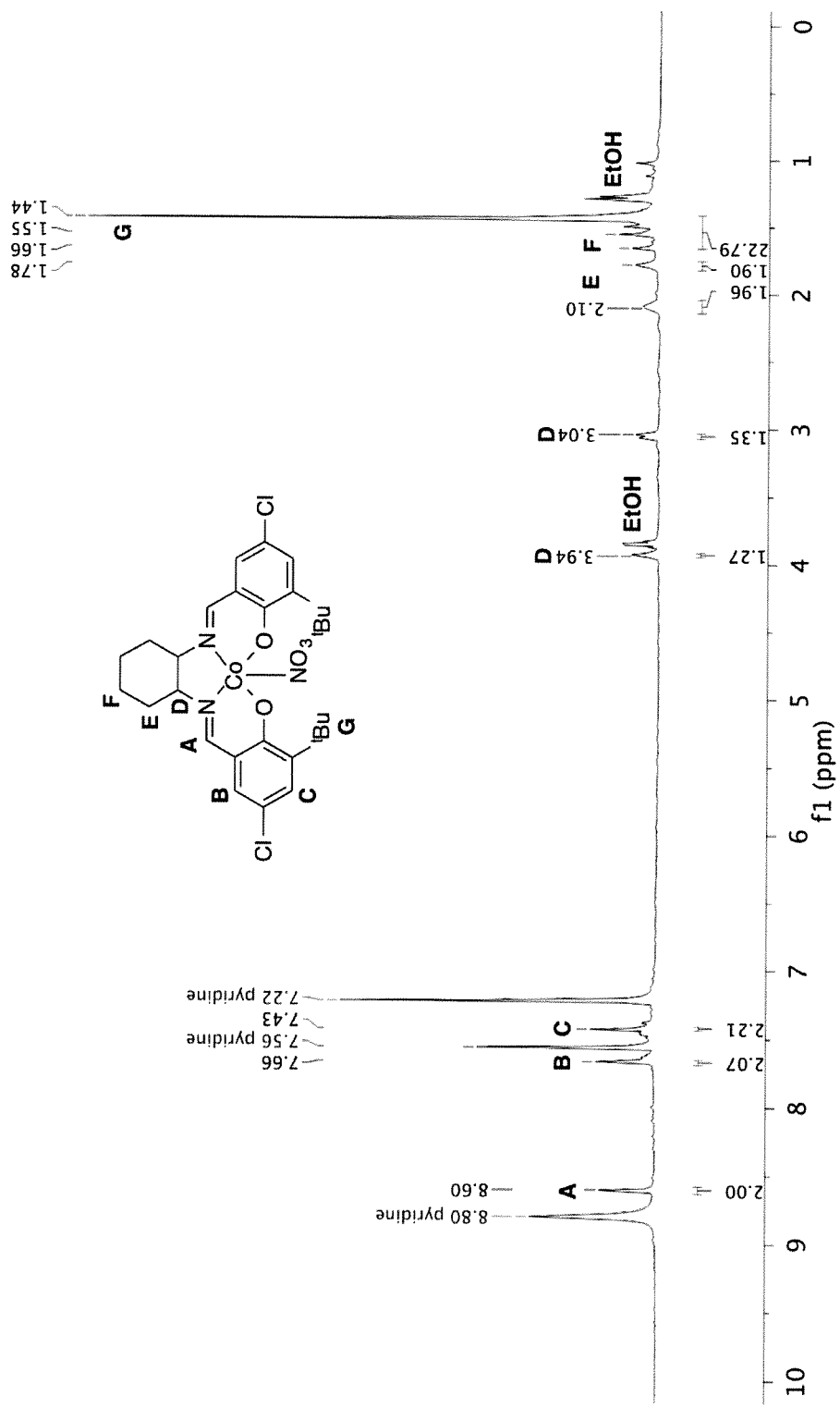
FIG. 7. $^1$H NMR spectrum of (R,R)—(Cl-salcy)CoNO$_3$ in C$_5$D$_5$N.
Figure 8:
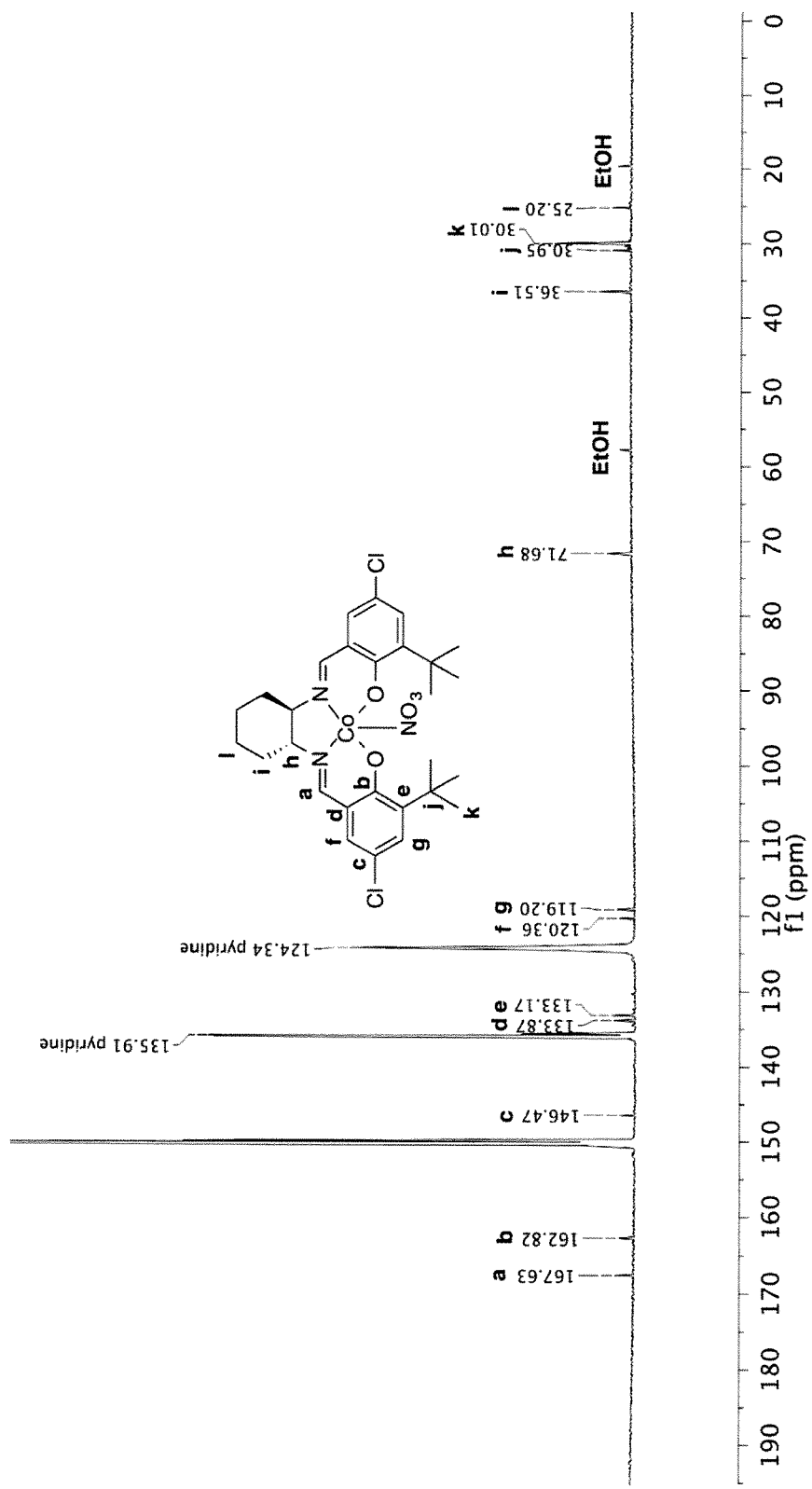
FIG. 8. $^{13}$C NMR spectrum of (R,R)—(Cl-salcy)CoNO$_3$ in C$_5$D$_5$N.

Both the (R,R) and (S,S) enantiomers of this catalyst were prepared. Only preparation of the (R,R) catalyst is described, as the only difference between the two is that the opposite enantiomer of the ligand is used to prepare the (S,S) catalyst. The yield represents average isolated yield. In a flame-dried Schlenk flask, N,N'-bis(3-tert-butyl-5-chloro-salicylidene)-1,2-cyclohexadiimine (0.500 g, 0.914 mmol) was dissolved in anhydrous, degassed dichloromethane under $N_2$ flow. In a second flame-dried Schlenk flask, $Co(NO_3)_2.6H_2O$ (0.293 g, 1.01 mmol) was dehydrated under reduced pressure until the color changed from red to light pink and subsequently dissolved in anhydrous, degassed methanol. The metal solution was then transferred to the ligand solution via cannula and the reaction mixture was stirred overnight while oxidizing under dry air with a drying tube charged with a dri-rite agent. Next the reaction mixture was evacuated to dryness and the resulting dark brown powder was rinsed with pentane and dried under reduced pressure at 60° C. and then stored in a glove box (78% isolated yield). $^1H$ NMR spectrum ($C_5D_5N$, 400 MHz): δ 8.60 (2H); 7.66 (2H); 7.43 (2H); 3.94 (1H); 3.04 (1H); 2.10 (2H); 1.78 (2H); 1.66 (2H); 1.55 (2H); 1.44 (18H) (FIG. 7). $^{13}C$ NMR spectrum ($C_5D_5N$, 125 MHz): δ 167.73; 162.82; 146.47; 133.87; 132.18;

120.36; 119.20; 71.68; 36.51; 30.95; 30.01; 25.20 (FIG. 8). HR/MS: calculated 559.1329 g/mol; found 559.1339 g/mol.

Figure 9:
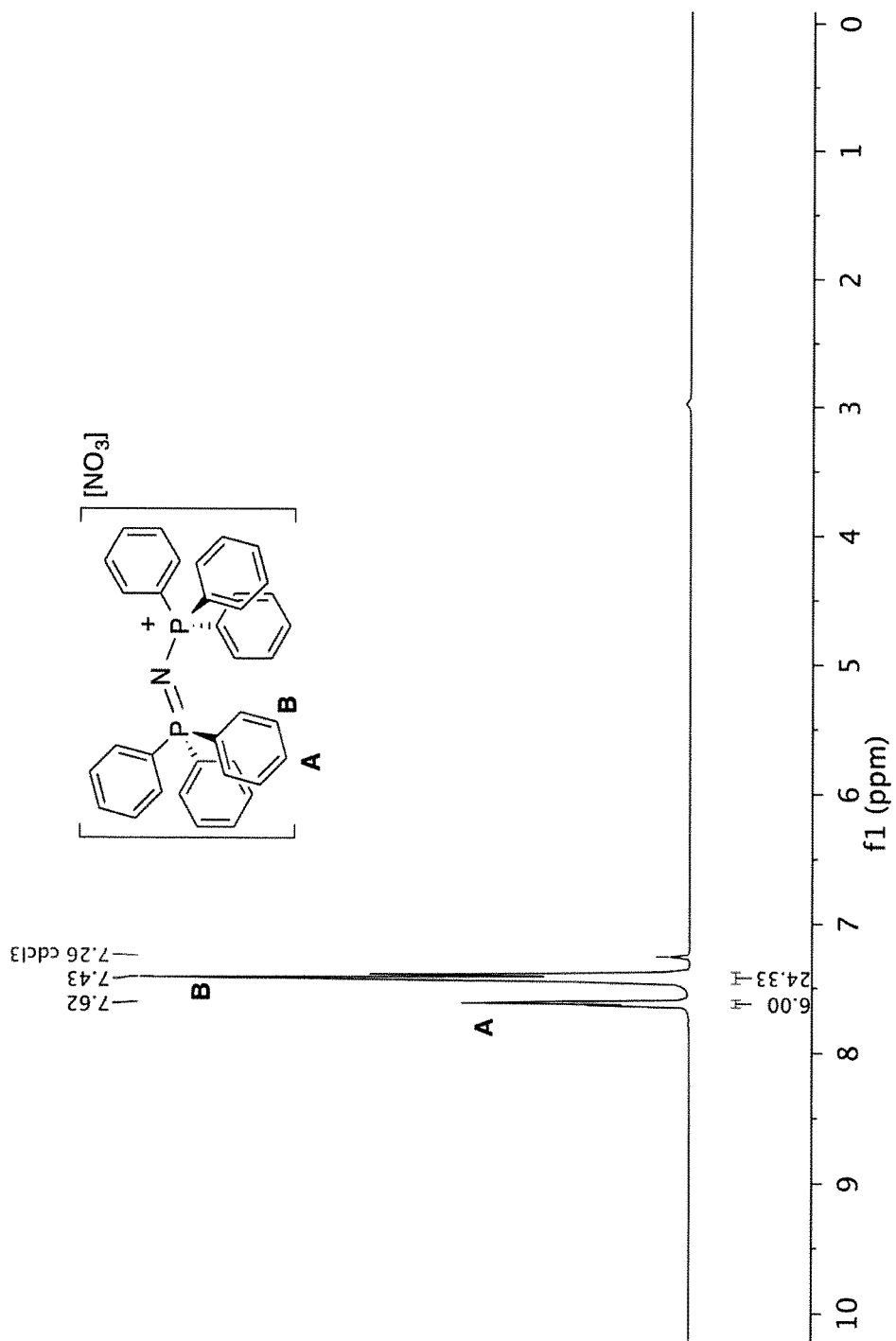
FIG. 9. $^1$H NMR spectrum of [PPN][NO$_3$] in CDCl$_3$.
Figure 10:
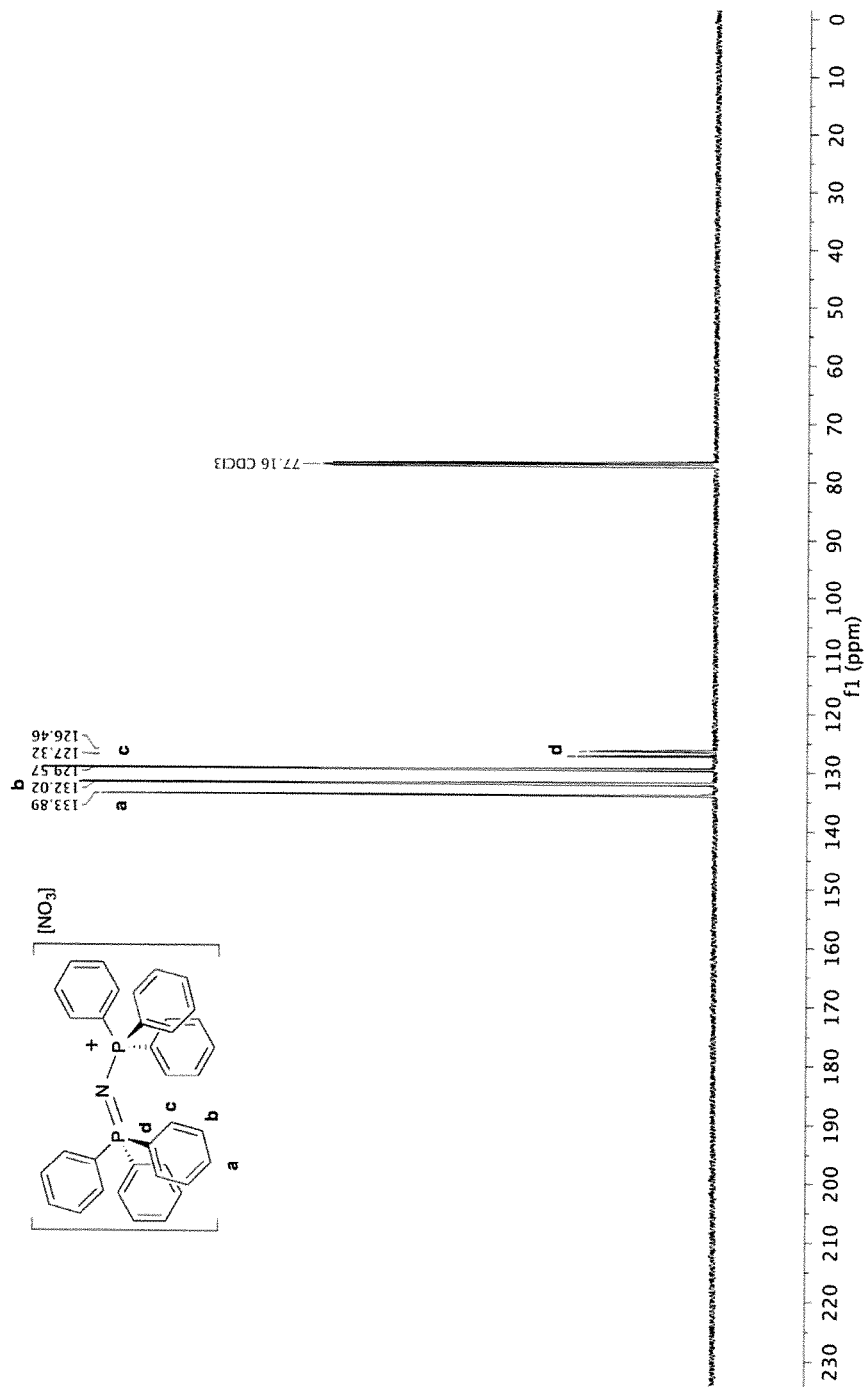
FIG. 10. $^{13}$C NMR spectrum of [PPN][NO$_3$] in CDCl$_3$.

Synthesis of [PPN][X] Salts. [PPN][NO$_3$]. Bis(triphenylphosphine)iminium chloride ([PPN]Cl) (3.00 g, 5.22 mmol) was dissolved in 70° C. deionized H$_2$O (75.0 mL), HNO$_3$ was added (0.360 mL, 5.74 mmol), and the reaction was slowly cooled to 25° C. A white precipitate formed immediately and the slurry was stirred for 1 hour. The resulting solid was collected by filtration, washed with warm water to remove residual acid and PPNCl and dried under reduced pressure at 60° C. for 24 hours (95% yield). Purity was assessed by $^1$H NMR spectroscopy to ensure removal of water and the presence of only one set of aryl peaks. A melting point of 230° C. was measured using differential scanning calorimetry, which matched well with the literature value. $^1$H NMR spectrum (CDCl$_3$, 400 MHz): δ 7.62 (m, 6H); 7.43 (m, 24H) (FIG. 9). $^{13}$C NMR spectrum (CDCl$_3$, 150 MHz): δ 133.89, 133.02, 129.57, 127.32/126.46 (d, J$_{CP}$=108 Hz) (FIG. 10). HR/MS: [NO$_3$] calculated 61.9878 g/mol; found 61.9870 g/mol.

Figure 11:
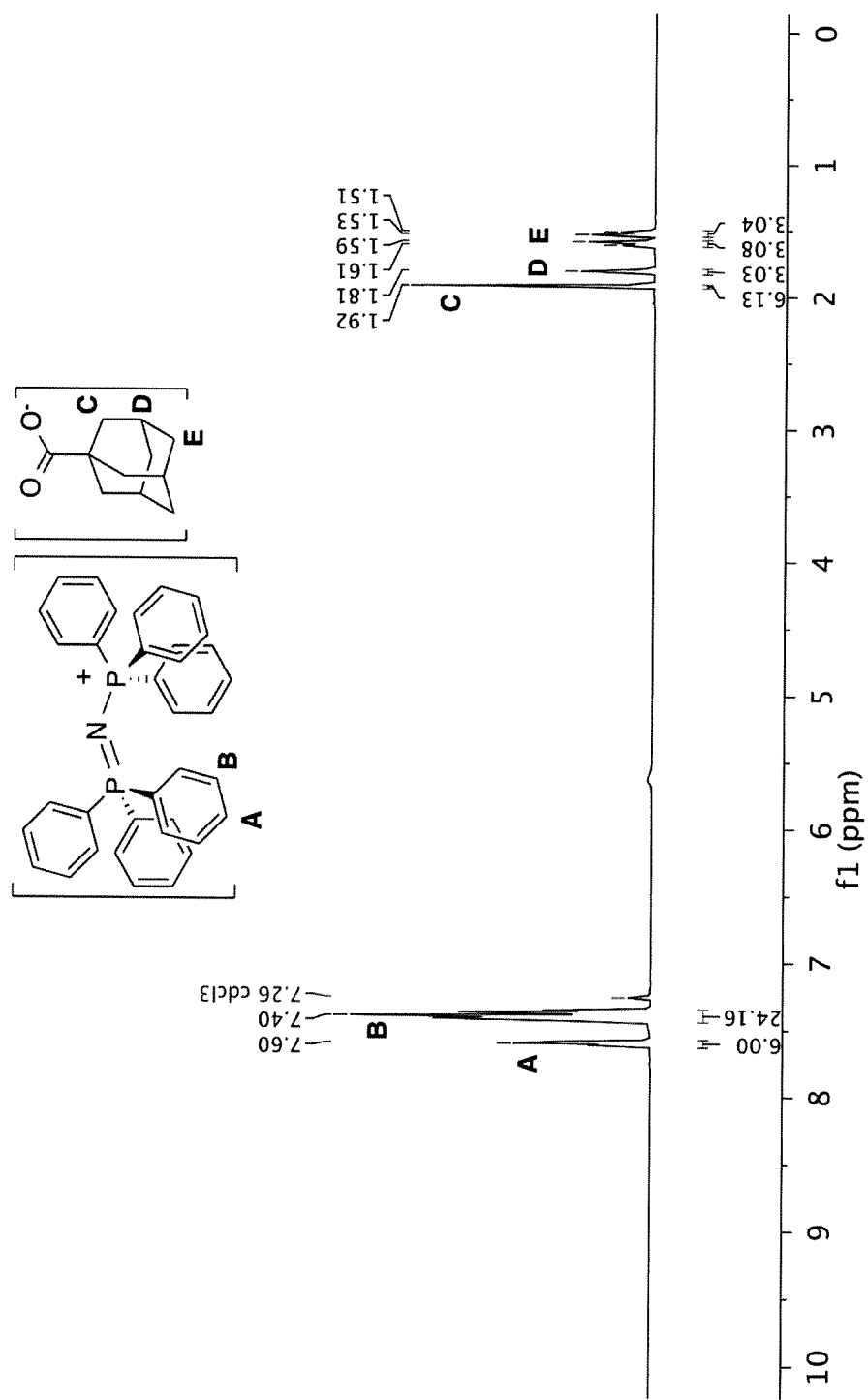
FIG. 11. $^1$H NMR spectrum of [PPN][1-Adamantate] in CDC$_3$.
Figure 12:
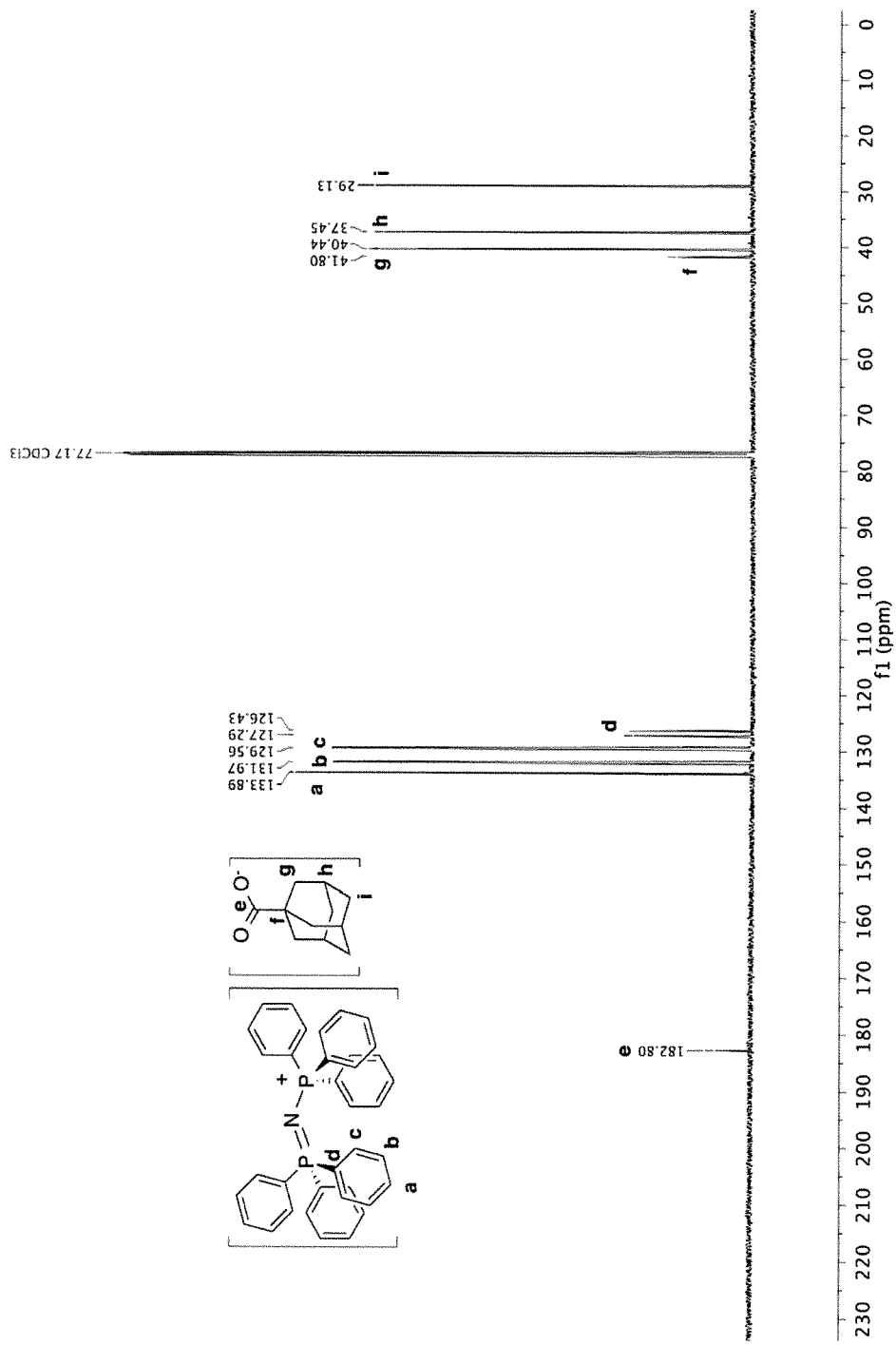
FIG. 12. $^{13}$C NMR spectrum of [PPN][1-Adamantate] in CDCl$_3$.

[PPN][1-Adamantate]. 1-Adamantanecarboxylic acid (0.314 g, 1.74 mmol) and NaOH (69.7 mg, 1.74 mmol) were added to a large vial and dissolved in 7.00 mL H$_2$O and 3.00 mL methanol by stirring with gentle heating. In a round bottom flask, [PPN]Cl (1.00 g, 1.74 mmol) was dissolved in 30.0 mL H$_2$O with stirring and the solution of 1-adamantanecarboxylic acid and NaOH was added to the flask and stirred while refluxing until the reaction was homogeneous. The reaction mixture was then cooled to room temperature with slow stirring. White crystals formed which were collected by filtration, rinsed with 0° C. H$_2$O, and dried at 40° C. under reduced pressure (82% yield). A melting point of 147° C. was measured using differential scanning calorimetry. $^1$H NMR spectrum (CDCl$_3$, 400 MHz): δ 7.60 (m, 6H); 7.40 (m, 24H); 1.92 (m, 6H); 1.81 (m, 3H); 1.61-1.59 (m, 3H), 1.53-1.51 (m, 3H) (FIG. 11). $^{13}$C NMR spectrum (CDCl$_3$, 150 MHz): δ 182.80, 133.89, 132.97, 129.56, 127.29/126.43 (d, J$_{CP}$=108 Hz), 41.80, 40.44, 37.45, 29.13 (FIG. 12). HR/MS: [1-Adamantate] calculated 179.1072 g/mol; found 179.1061 g/mol.

Figure 13:
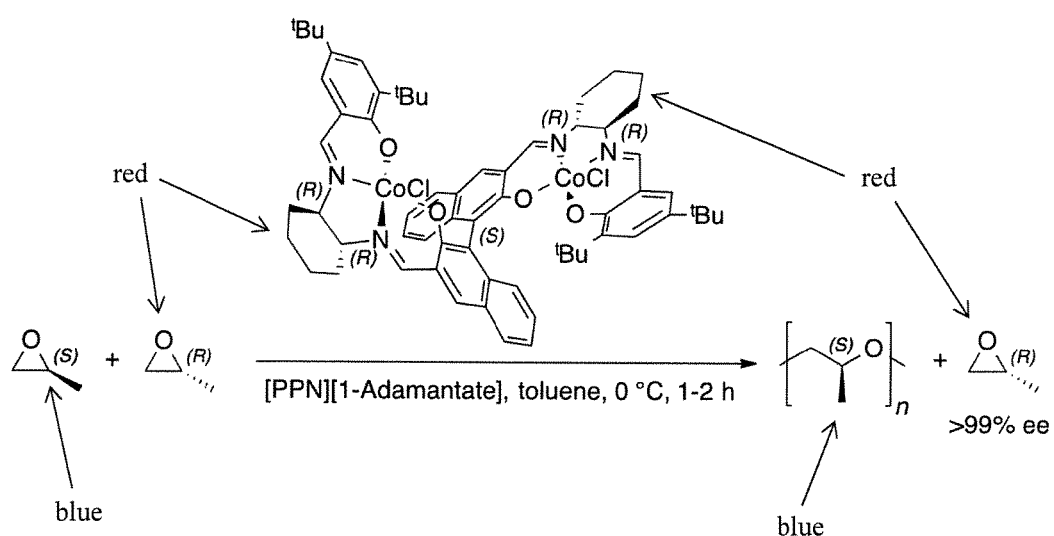
FIG. 13. Example of use of (R,R,S,R,R)-Bimetallic cobalt salen catalyst for the resolution of (R)-propylene oxide from racemic propylene oxide via enantioselective polymerization of (S)-propylene oxide.

Resolution of (S)-Propylene Oxide and (R)-Propylene Oxide. Both (S)- and (R)-propylene oxide were resolved from racemic propylene oxide using a bimetallic cobalt salen catalyst that enantioselectively polymerizes only one enantiomer of epoxide, allowing the other enantiomer to be collected in high enantiomeric excess (ee) (FIG. 13). Both the (R,R,S,R,R) and (S,S,R,S,S) versions of this catalyst were synthesized as reported in previous literature, where the former was used to prepare (R)-propylene oxide and the latter to prepare (S)-propylene oxide from racemic propylene oxide. In a glove box, the appropriate enantiomer of the catalyst (6.60 mg, 5.75 µmol) and [PPN][1-Adamantate] (8.30 mg, 12.0 mol) were added to a flame-dried vial equipped with a Teflon coated stir bar. The solids were then dissolved in 11.5 mL toluene (to form a 2M solution), and the vial capped with a Teflon-lined, puncturable top. The racemic epoxide was measured out in an airtight syringe, sealed with a rubber septum, and removed from the glove box along with the catalyst solution.

The vial containing the catalyst/cocatalyst solution was cooled in an ice bath for 15 minutes and then the epoxide was injected into the reaction mixture. The reaction mixture was then stirred for 1-2 hours in the ice bath, and aliquots were analyzed for conversion via $^1$H NMR spectroscopy. Both enantiomers of this bimetallic catalyst are very highly enantioselective, so once >50% conversion to polymer was attained, the remaining enantiopure epoxide starting material was collected via vacuum transfer into a small, thick-walled Schlenk flask cooled with liquid N$_2$. The propylene oxide was then analyzed by gas chromatography as described above. Both (S)- and (R)-propylene oxide were obtained with >99% ee.

Representative Synthesis of Isotactic Poly((S)-propylene succinate) with (R,R)—(Cl-salcy)CoNO$_3$. In a glove box, a flame-dried 30 mL vial equipped with a Teflon coated stir bar was charged with (R,R)—(Cl-salcy)CoNO$_3$ (3.11 mg, 5.00 µmol), [PPN][NO$_3$] (3.00 mg, 5.00 µmol), and succinic anhydride (200 mg, 2.00 mmol). (S)-Propylene oxide (0.280 mL, 4.00 mmol) was added via syringe with care to wash all solids from the side of the vial. The vial was sealed with a Teflon lined cap, removed from the glove box, and placed in an aluminum heat block preheated to 30° C. Initially, the reaction mixture was heterogeneous, with the solid succinic anhydride dissolving over time until the mixture became homogeneous, around 24 hours after the reagents were combined. Over the course of 48 hours, the reaction mixture became viscous, at which point the vial was removed from the heat block, and the mixture was dissolved in 4 mL dichloromethane and precipitated into 20 mL hexanes. The hexanes were decanted and the polymer dried in vacuo. The polymer was then dissolved again in 4 mL dichloromethane and 20 mL methanol was added dropwise over 5-10 minutes with vigorous stirring until a white precipitate formed. After allowing time for the solid to settle, the methanol was decanted and the polymer dried in vacuo. Poly((R)-propylene succinate) was synthesized in the same manner, substituting (R)-propylene oxide for the (S)-propylene oxide.

Figure 14:
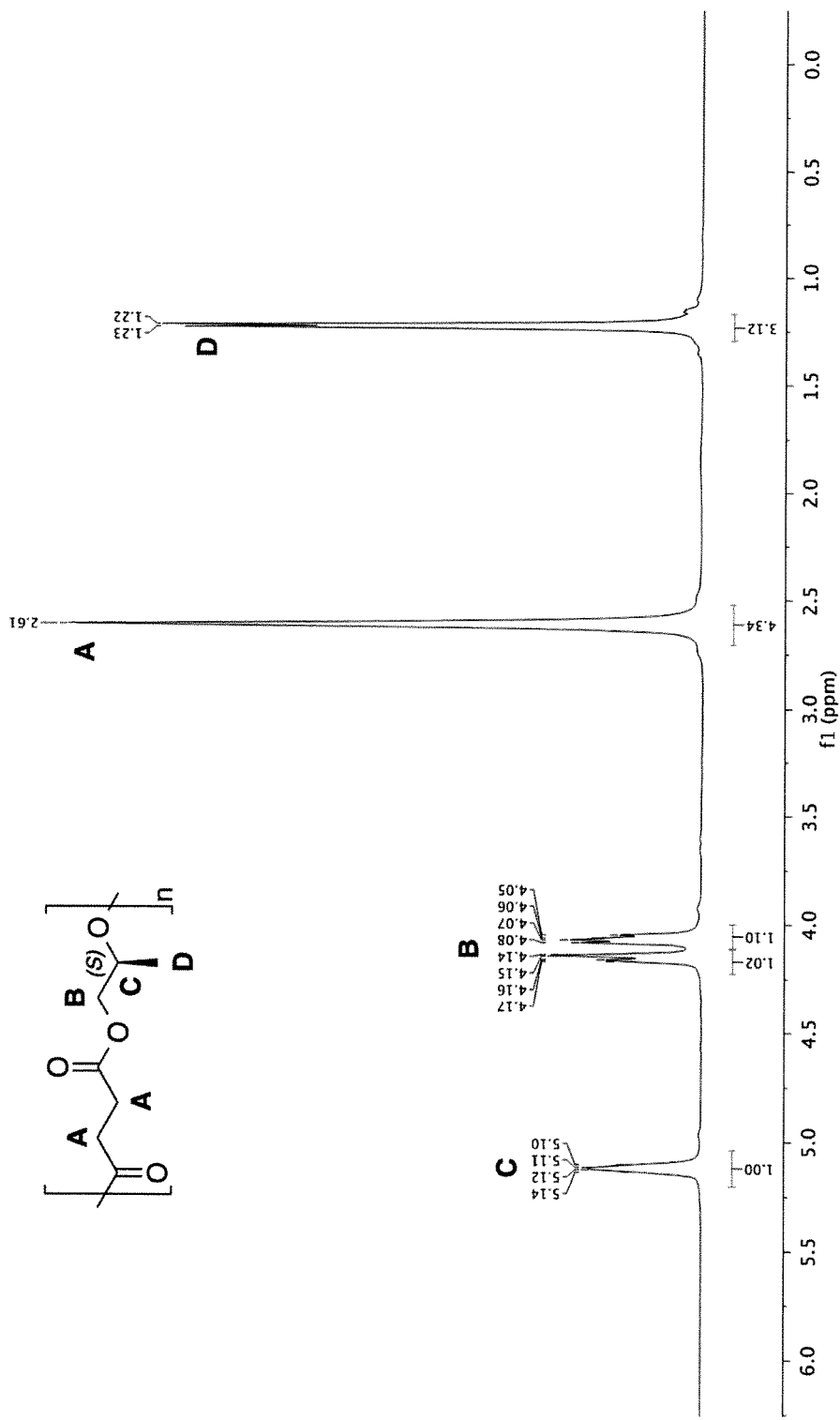
FIG. 14. $^1$H NMR spectrum of poly((S)-propylene succinate) in CDCl$_3$.
Figure 15:
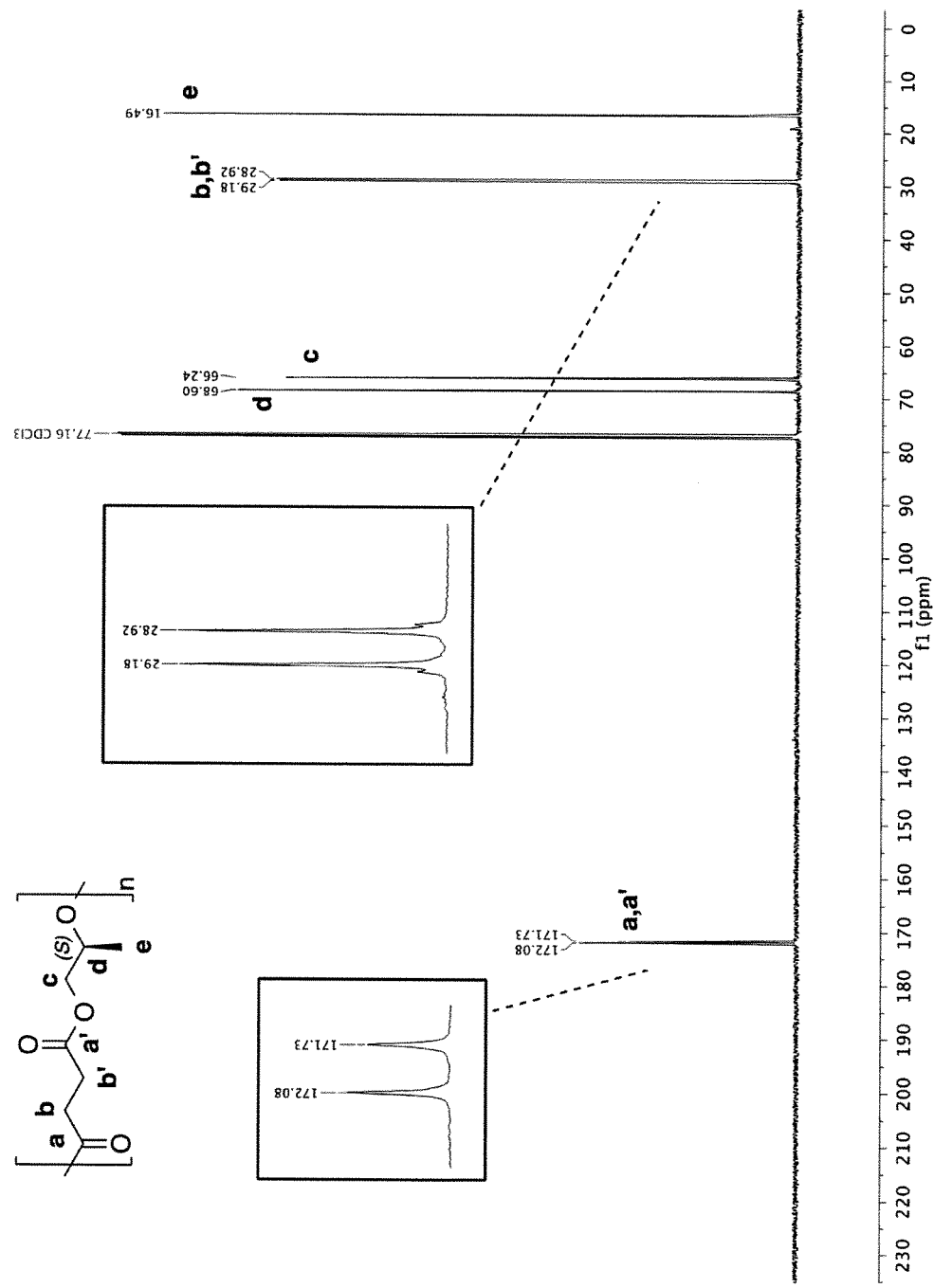
FIG. 15. $^{13}$C NMR spectrum of poly((S)-propylene succinate) in CDCl$_3$.

NMR Spectra and Peak Assignments for Isotactic (S)-Poly(propylene succinate). $^1$H NMR spectrum (CDCl$_3$, 500 MHz): δ 5.12 (m, 1H); 4.17-4.14 (dd, J=3.8, 11.5 Hz, 1H); 4.08-4.05 (dd, J=6.3, 11.5 Hz, 1H); 2.61 (bm, 4H); 1.22 (d, J=6.3, 3H) (FIG. 14). $^{13}$C NMR spectrum (CDCl$_3$, 150 MHz): δ 172.08; 171.73; 68.60; 66.24; 29.18; 28.92; 16.49 (FIG. 15). $^1$H and $^{13}$C NMR spectra of poly((R)-propylene succinate) look identical to those of the poly((S)-propylene succinate) pictured below.

Figure 17:
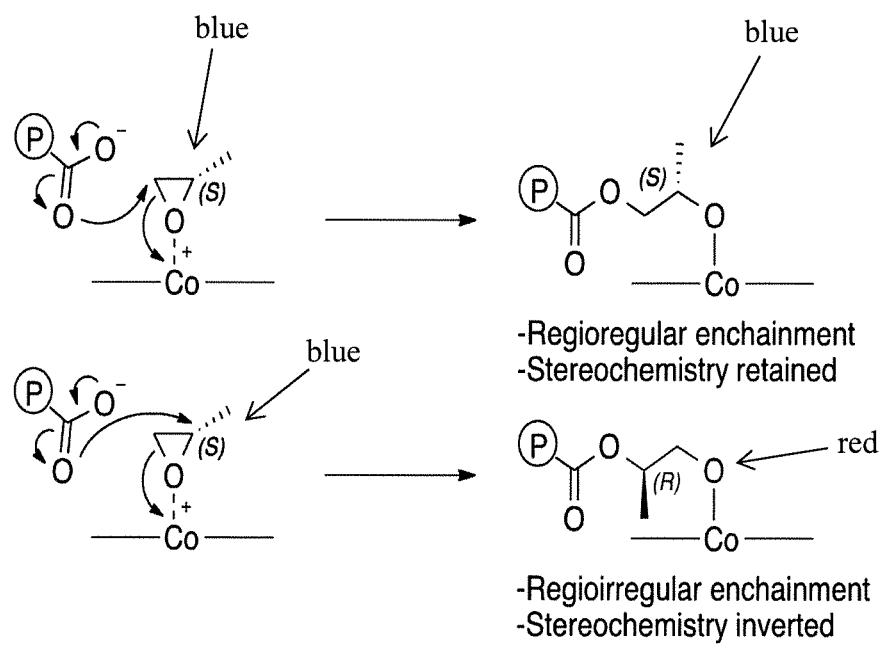
FIG. 17. Example of regio- and stereochemistry of the epoxide ring-opening step.

Determination of Regioregularity via Gas Chromatography. In the ring-opening alternating copolymerization of succinic anhydride and propylene oxide, the regiochemistry is determined by the directionality of the ring-opening of the epoxide. In general, the epoxide is opened at the less sterically hindered methylene carbon, and a regioerror occurs when the epoxide is opened at the methine carbon instead (FIG. 17). Because of the S$_N$2 nature of the ring-opening step, attack at the methine carbon not only results in a regioerror but a stereoerror as well. This means that the regioregularity of the polymerization can be assessed by determining the enantiopurity of polymers synthesized from enantiopure starting materials. Given the propylene oxide starting material has an ee of >99%, then the closer the diols are to ee's of 99%, the more regioregular they are. The regioregularity of poly(propylene succinate) polymers synthesized with (Cl-salcy)CoNO$_3$ was analyzed using gas chromatography after degradation and derivatization as described below.

Degradation of Poly(Propylene Succinate)

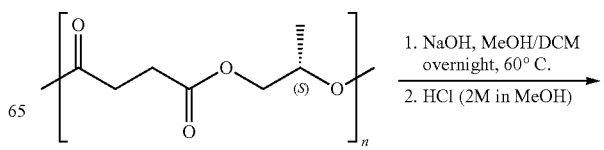

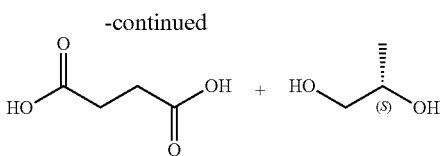

To determine the enantiopurity of poly(propylene succinate) polymerized from enantiopure propylene oxide, the polymer was first degraded to propylene glycol, a process that does not affect the existing stereocenters. Approximately 200-300 mg of (S)- or (R)-poly(propylene succinate) were dissolved in 3.0 mL dichloromethane, 15 mL methanol and 200 mg NaOH were added, and the reaction mixture was stirred at 60° C. for 12 hours. The reaction mixture was then neutralized with acidic methanol (2M HCl in MeOH) and the solvent evacuated under reduced pressure. Diethyl ether (40 mL) was added to the resulting off-white powder and the slurry was vigorously stirred for 1 hour, followed by filtration and removal of the solvent to yield propylene glycol.

Derivatization of Diols Resulting from Degradation.

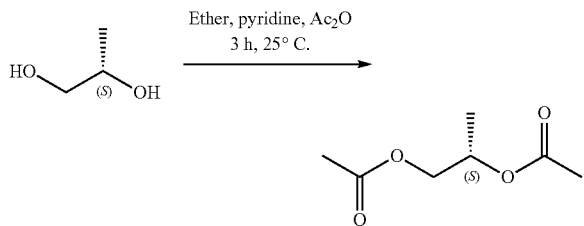

To separate the propylene glycol enantiomers on a chiral gas chromatography column, they were derivatized with acetic anhydride to the methyl esters. Into a small vial equipped with a Teflon lined stir bar was added 1 mL diethyl ether and equal amounts (5-10 drops) propylene glycol, pyridine, and acetic anhydride. The reaction mixture was stirred 3 hours at room temperature, washed with deionized H$_2$O (3×1 mL) and dried over Na$_2$SO$_4$. The derivatized product was then analyzed via gas chromatography. The diacetate was obtained with an ee of 97% when (R,R)—(Cl-salcy)CoNO$_3$ was used, and with an ee of 96% when (S,S)—(Cl-salcy)CoNO$_3$ was used, indicating that both enantiomers produced highly regioregular poly(propylene succinate).

The enantiomeric ratio, calculated from the % ee, can in turn be used to determine the percent head-to-tail linkages (% HT) in the polymer chains. For every stereoerror present (indicating a regioerror is also present), there will be one head-to-head (HH) and one tail-to-tail (TT) linkage. With this information, the % HT can be calculated, and in fact it corresponds with the % ee. For example, a sample with 0% ee has an enantiomeric ratio of 50:50. In 100 repeat units of this polymer (100 possible HT linkages), there will be 50 stereoerrors, corresponding to 50 HH linkages and 50 TT linkages, and therefore 0% HT linkages.

Determination of Catalyst Enantiomer/Epoxide Enantiomer Combinations. To determine which enantiomer of catalyst should be used to copolymerize each enantiomer of propylene oxide with succinic anhydride, racemic propylene oxide was polymerized with both (R,R)—(Cl-salcy)CoNO$_3$ and (S,S)—(Cl-salcy)CoNO$_3$ as described above, except that a puncturable Teflon lined cap was used. When the reaction mixtures became viscous, the excess epoxide was collected via vacuum transfer into a small, thick-walled Schlenk flask cooled with liquid N$_2$. The propylene oxide was then analyzed by gas chromatography. For (R,R)—(Cl-salcy)CoNO$_3$, a slight preference for (S)-propylene oxide was observed, as the starting propylene oxide was enriched in (R)-propylene oxide, while the opposite was observed when (S,S)—(Cl-salcy)CoNO$_3$ was used. In both cases, a k$_{rel}$ of around 4 was observed where the catalyst showed slightly greater activity for polymerizing the opposite enantiomer of propylene oxide.

Additionally, both (S)-propylene oxide and (R)-propylene oxide were polymerized using both (R,R)—(Cl-salcy)CoNO$_3$ and (S,S)—(Cl-salcy)CoNO$_3$, and the regiochemistry of the resulting poly(propylene succinate) was analyzed as described above. For both enantiomers of propylene oxide, polymerization with the opposite enantiomer catalyst gave higher regioregularity, around 97% HT linkages, as opposed to 86% HT linkages when the matching enantiomer of catalyst and epoxide were used.

Figure 16:
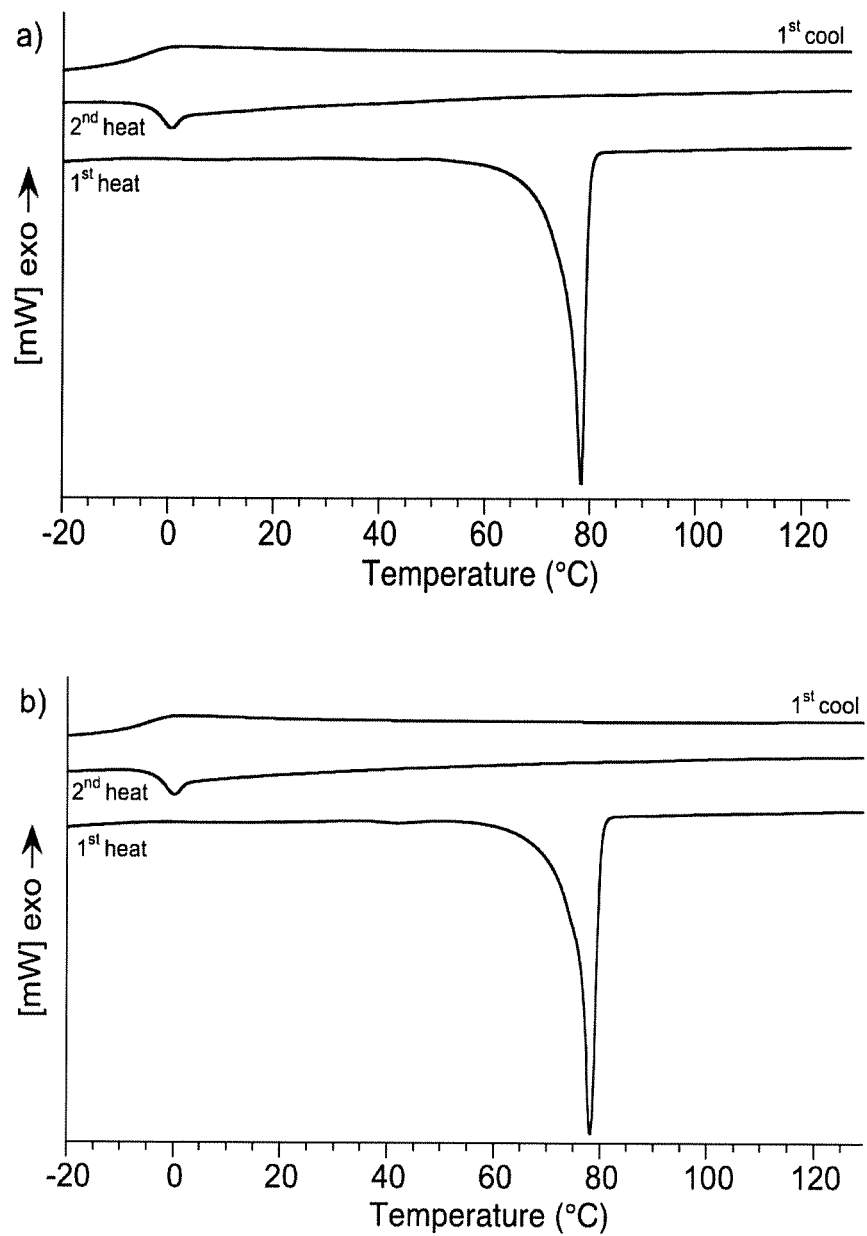
FIG. 16. DSC thermograms of a) poly(S)- and b) poly((R)-propylene succinate) after precipitation with methanol.

Polymer Precipitation and DSC Procedures. Poly(S)- and poly((R)-propylene succinate) both show no crystallinity from the melt by differential scanning calorimetry (DSC). Crystallinity, and therefore a melting temperature (T$_m$) of these polymers, is seen only if the polymer is precipitated with methanol, a method that is impractical for industrial applications as the resulting polymer is a very fine powder. For this method, each polymer was dissolved in 4.0 mL dichloromethane and 20.0 mL methanol was added dropwise over 5-10 minutes with vigorous stirring until a white precipitate formed. After allowing time for the precipitate to settle, the solvent was decanted and the polymer dried in vacuo at 60° C. DSC thermograms of the precipitated polymers show that after precipitation, the T$_m$ for both samples (FIGS. 16a and 16b) can be seen to be 78° C., with ΔH values of 68 J/g and 78 J/g for poly((S)-propylene succinate) and poly((R)-propylene succinate), respectively (FIGS. 16a and 16b). The T$_m$, however, is only observed on the first heat, with no immediate recrystallization upon cooling. Regardless of the rate of heating/cooling (10° C./min or 2° C./min) or the temperature to which the sample was heated (90° C., 130° C., or 200° C.), the T$_m$ remained the same and no recrystallization was observed.

Figure 18:
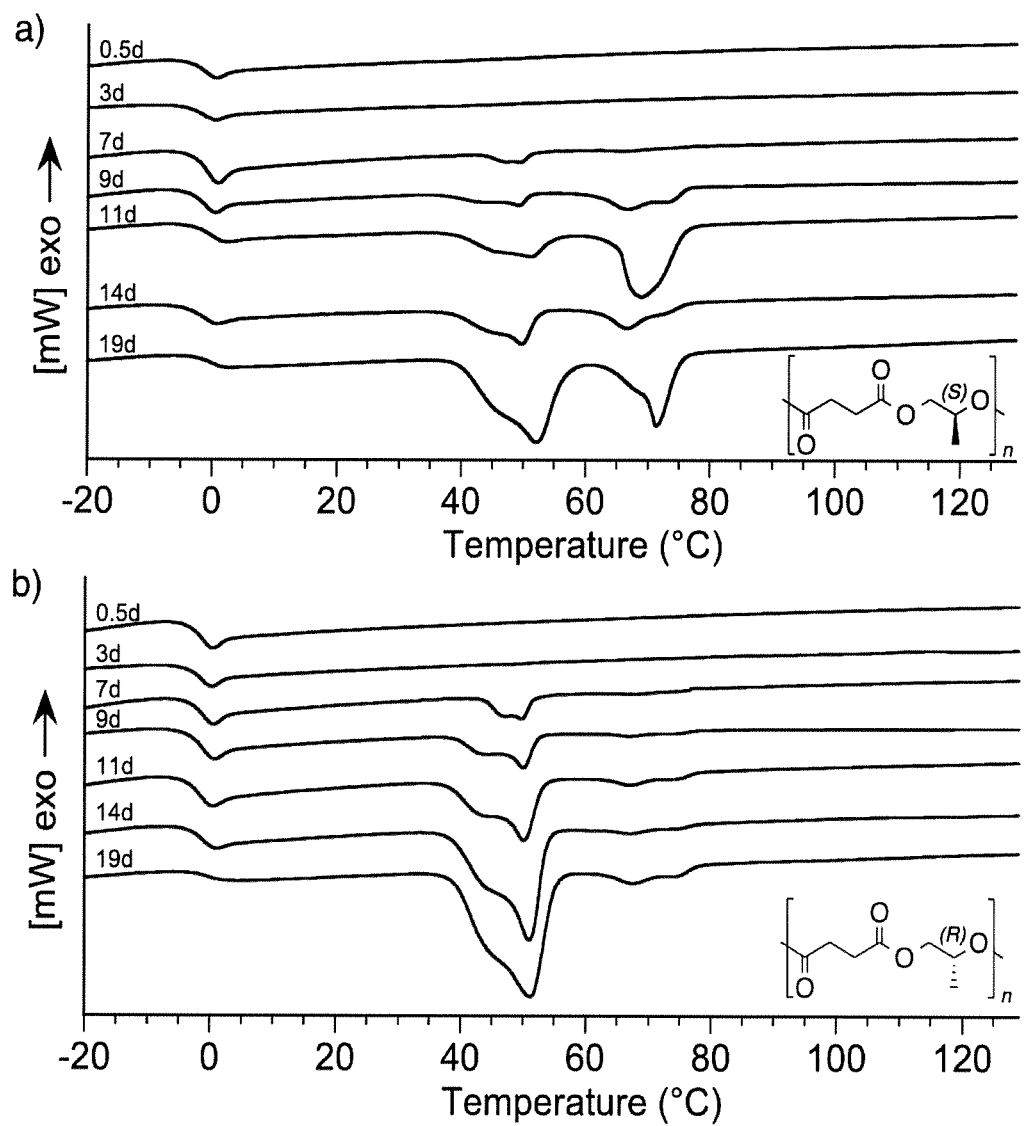
FIG. 18. Crystallization of a) poly((S)-propylene succinate) and b) poly((R)-propylene succinate) over time.

Crystallization of poly((S)-propylene succinate) and poly((R)-propylene succinate). To determine the amount of time required for poly((S)-propylene succinate) and poly((R)-propylene succinate) to crystallize from the melt, approximately 200 g of each polymer were melted at 130° C. The samples were then allowed to sit at room temperature, and DSC was performed on aliquots from these samples with a heating rate of 10° C./min several times over the course of 19 days (FIGS. 18a and 18b). For both samples, the T$_m$ first reappeared after 7 days, although at a lower temperature than is seen before melting (around 40-50° C.). Over time, a higher melting polymorph (around 70° C.) returns to some extent in both samples, although much more of this polymorph is observed in the poly((S)-propylene succinate) sample. It is currently unclear why the poly((S)-propylene succinate) and poly((R)-propylene succinate) recrystallized differently from the melt, although precipitation of both of these polymers with methanol gave the same T$_m$. Plotting ΔH versus time allowed a T$_{1/2}$ to be extrapolated for the recrystallization time of each enantiopure sample and for the stereocomplex. Initial data suggests that the stereocomplex recrystallizes approximately three orders of magnitude faster than either poly((S)-propylene succinate) or poly((R)-propylene succinate). Further kinetic studies on the recrystallization rate of both species are ongoing.

Stereocomplex Formation and DSC Analysis. The poly(propylene succinate) stereocomplex was formed via two methods which were compared by DSC and powder X-ray diffraction. For method 1, 40-50 mg each of poly(S)- and poly((R)-propylene succinate) were dissolved in ~1.5 mL dichloromethane and mixed together by shaking in a small vial. The top of the vial was then covered with Parafilm, punctured with one hole, and the solvent was allowed to evaporate slowly and completely. The material was then dried in vacuo to ensure all solvent was removed. For method 2, the stereocomplex was made as in method 1, dissolved in minimal dichloromethane, and precipitated again by adding methanol dropwise with vigorous stirring.

Figure 19:
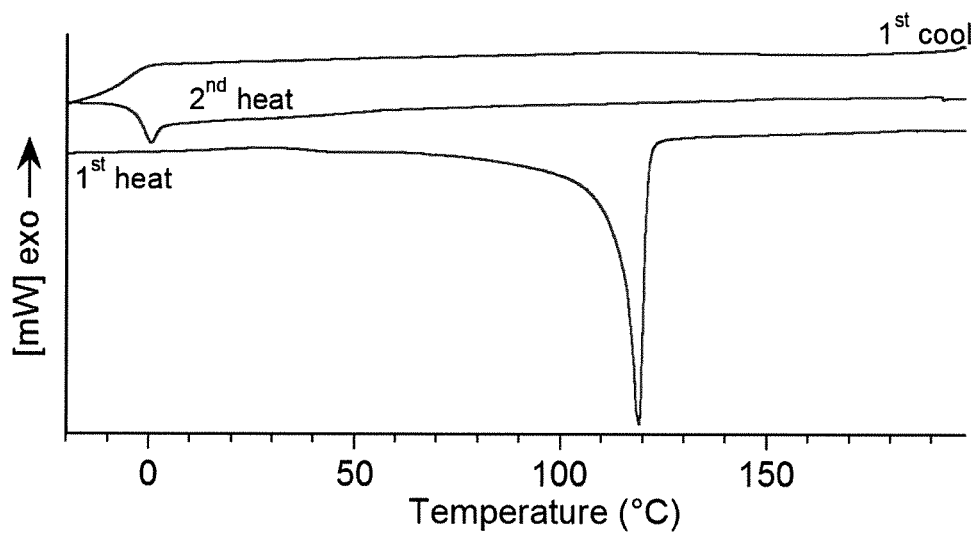
FIG. 19. DSC thermogram of the poly(propylene succinate) stereocomplex formed by solvent evaporation, with a heating rate of 10° C./min and heating to 200° C.
Figure 20:
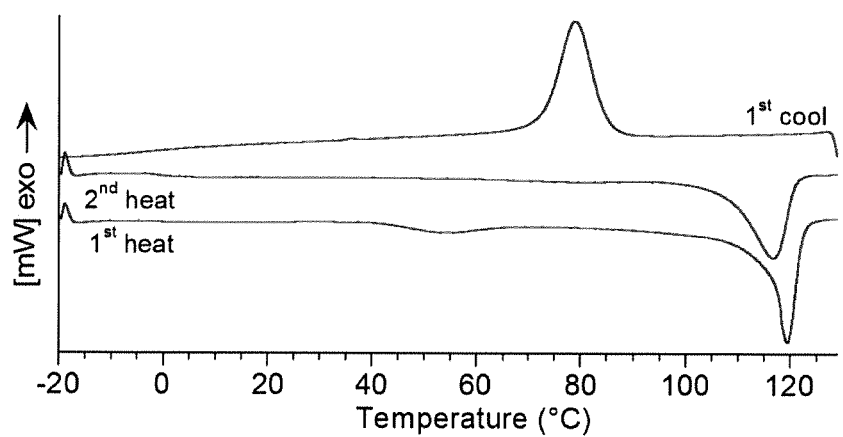
FIG. 20. DSC thermogram of the poly(propylene succinate) stereocomplex formed by precipitation with methanol, with a heating rate of 10° C./min and heating to 130° C.
Figure 21:
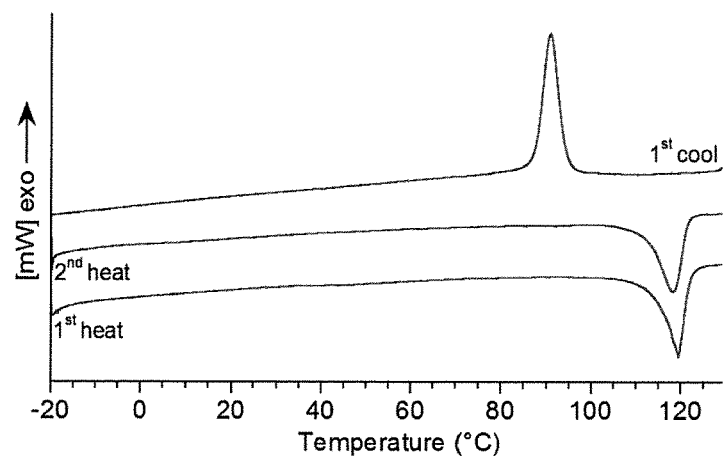
FIG. 21. DSC thermogram of the poly(propylene succinate) stereocomplex formed by precipitation with methanol, with a heating rate of 2° C./min and heating to 130° C.

With a heating rate of 10° C./min and heating to 200° C., the polymer stereocomplex of poly((S)-propylene succinate) and poly((R)-propylene succinate) exhibited an increased $T_m$ in comparison to the enantiomerically pure polymers (119° C., $\Delta H=88$ J/g). However, as shown in FIG. 19, no recrystallization is observed upon cooling and no $T_m$ is seen on the second heat. To induce crystallization in the polymer stereocomplex, the polymer was first precipitated with methanol as described above for the enantiomerically pure polymers, and then the sample was heated at a rate of 10° C./min to only 130° C. and subsequently cooled at the same rate. FIG. 20 shows that with this procedure, recrystallization is observed as well as melting during the second heat. The recrystallization temperature of the stereocomplex can be further optimized by heating and cooling at a rate of 2° C./min and heating only to 130° C., as shown in FIG. 21. In this case, again, the $T_m$ remains the same but the recrystallization temperature increases from 80° C. to 90° C.

Additionally, when the stereocomplex recrystallizes upon cooling, no glass transition ($T_g$) is observed during the second heat. It is expected that the slower the rate of heating (2° C./min versus 10° C./min) will result in smaller $T_g$. However, when the stereocomplex is cooled slowly at 2° C./min to induce recrystallization, and subsequently heated at 10° C./min, there is still no visible $T_g$, suggesting that the crystallized stereocomplex has a high degree of crystallinity. Determination of the percent crystallinity of the poly(propylene succinate) stereocomplex is currently underway.

Figure 22:
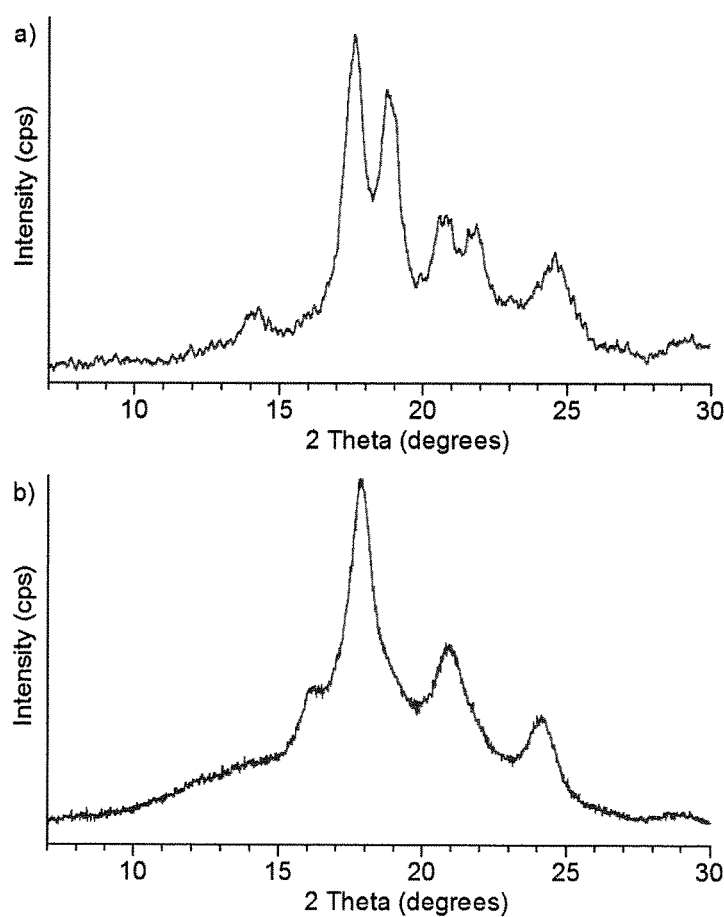
FIG. 22. Powder X-ray diffraction profiles for a poly(propylene succinate) stereocomplex formed by a) mixing and solvent evaporation (method 1) and b) solvent evaporation and subsequent precipitation into methanol (method 2) as described above.

Powder X-ray Diffraction of PPS Stereocomplex. The powder X-ray diffraction profile for the poly(propylene succinate) stereocomplex varied depending on the method of stereocomplex formation, via solvent evaporation or precipitation from methanol as described above (FIG. 22). When solvent evaporation (method 1) was used, six peaks were observed at 14.30, 17.6°, 18.8°, 21.0°, 21.9°, and 24.6°. In contrast, when precipitation from methanol (method 2) was used for stereocomplex formation, only four peaks were observed at 16.20, 17.9°, 20.8°, and 24.1°. As can be seen in FIG. 22, while the exact locations of the major peaks differ for the two methods, the general locations and relative intensities of the peaks are the same. Both profiles are different from those of poly(S)- and poly((R)-propylene succinate) alone, and we predict that the doubling of the peaks when method 1 is used for stereocomplex formation is a result of the presence of two polymorphs in the sample.

Example 2

This example provides an example of characterization of compositions of the present disclosure.

Parent Polymer Ratio and Stereocomplex Formation. To investigate the range of ratios of (S)- to (R)-poly(propylene succinate) that show stereocomplexation, mixtures of (S):(R) polymers in ratios of 50:50, 60:40, 70:30, and 90:10 were analyzed by differential scanning calorimetry (DSC). Samples of (S)- and (R)-poly(propylene succinate) were dissolved in dichloromethane at a concentration of 25 mg/mL, combined, and the solvent allowed to evaporate slowly overnight.

Figure 23:
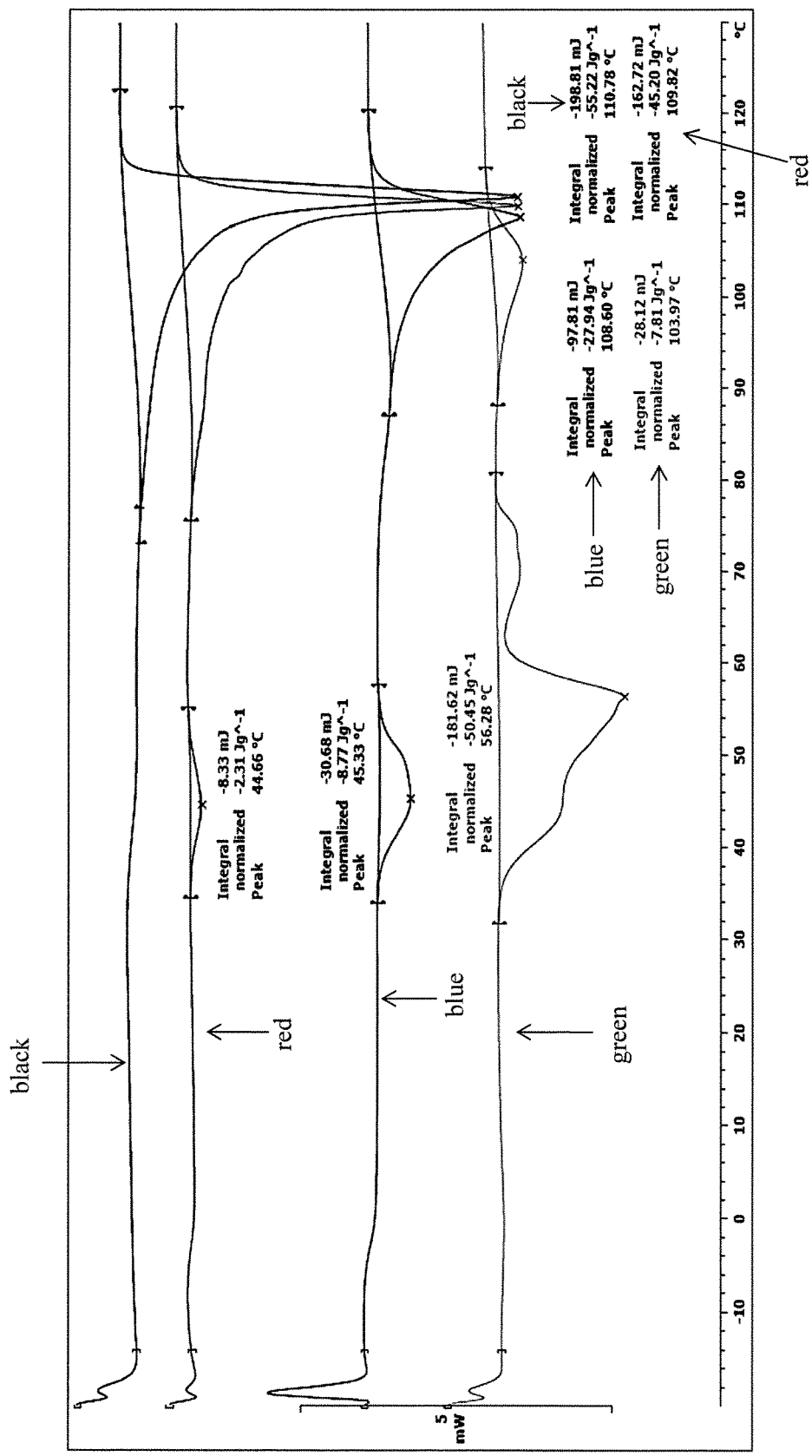
FIG. 23. A comparison of the thermal properties of four ratios of (S)- to (R)-poly(propylene succinate) (50:50 (black), 60:40 (red), 70:30 (blue), and 90:10 (green)). The 50:50 mixture (in black) shows the highest T$_m$, around 110° C., and the highest stereocomplex enthalpy of 55 J/g. As shown in red, the 60:40 mixture shows a T$_m$ only one degree lower, and an enthalpy of 45 J/g. Additionally, a small amount of homocrystallinity can be observed around 45° C., suggesting that the small amount of(S)-poly(propylene succinate) in excess still crystallizes by itself.

FIG. 23 shows a comparison of the thermal properties of each combination (50:50 (black), 60:40 (red), 70:30 (blue), and 90:10 (green)). The 50:50 mixture (in black) shows the highest $T_m$, around 110° C., and the highest stereocomplex enthalpy of 55 J/g. As shown in red, the 60:40 mixture shows a $T_m$ only one degree lower, and an enthalpy of 45 J/g. Additionally, a small amount of homocrystallinity can be observed around 45° C., suggesting that the small amount of (S)-poly(propylene succinate) in excess still crystallizes by itself.

The 70:30 (in blue) and 90:10 (in green) mixtures support this trend, with increasing amounts of homopolymer crystallinity observed as the excess of (S)-poly(propylene succinate) increases. The enthalpy of the stereocomplex crystallites decreases to 28 J/g and 8 J/g, respectively, as less (R)-poly(propylene succinate) is available. However, stereocomplexation still occurs even with very small amounts of the second enantiomer present, and the $T_m$ drops by only a few degrees, to 107° C. in the 70:30 mixture and to 102° C. in the 90:10 mixture. Compositions with an excess of (R)-poly(propylene succinate) would be expected to show the same results.

Example 3

This example provides an example of characterization of compositions of the present disclosure.

Epoxide Enantiopurity and Stereocomplex Formation. To investigate the poly(propylene succinate) enantiopurity required for stereocomplex formation, both (S)- and (R)-poly(propylene succinate) were synthesized using propylene oxide of varying enantiopurity, from 60-80% enantiomeric excess of (S)- and (R)-propylene oxide, respectively. The resulting (S)- and (R)-polymers with matching enantiopurity of 60, 70, and 80% were then combined by dissolving in dichloromethane, mixing, and allowing the solvent to evaporate slowly overnight. Differential scanning calorimetry (DSC) was used to analyze the thermal properties of the stereocomplexes formed. For comparison, the stereocomplex formed from propylene oxide with >99% enantiomeric excess has a $T_m$ of 118° C., and recrystallizes at 90° C.

Figure 24:
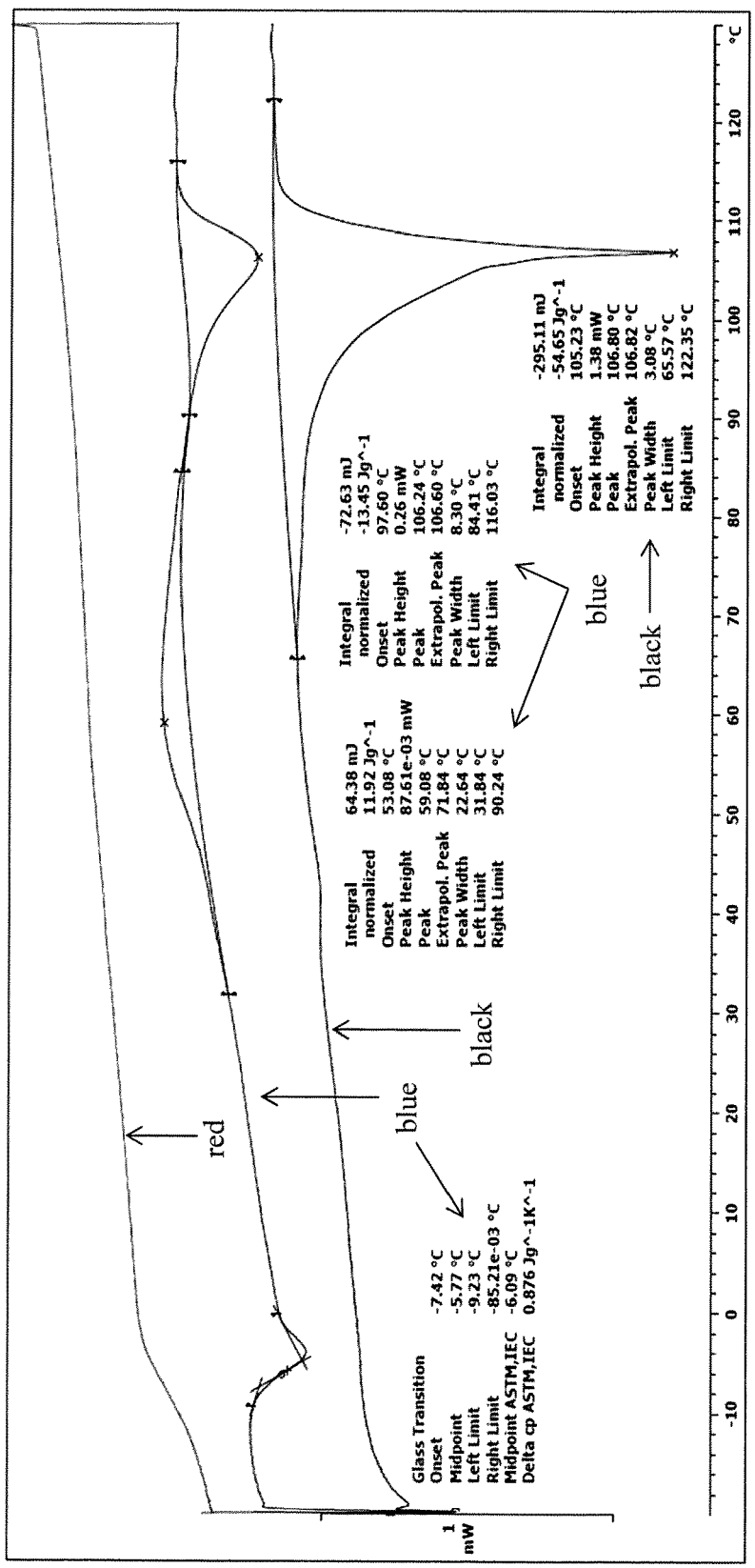
FIG. 24. Thermal properties of a stereocomplex formed from (S)- and (R)-poly(propylene succinate) of 80% enantiomeric excess. Black line is the first heat. Red line is cooling. Blue line is second heat.

FIG. 24 shows the stereocomplex formed from (S)- and (R)-poly(propylene succinate) of 80% enantiomeric excess. The first heat (in black) shows a $T_m$ of 107° C., lower than that of the original stereocomplex, but still much higher than (S)- or (R)-poly(propylene succinate) alone. Recrystallization does not occur immediately upon cooling (in red), but to some extent does occur during the second heat (in blue, around 58° C.).

Figure 25:
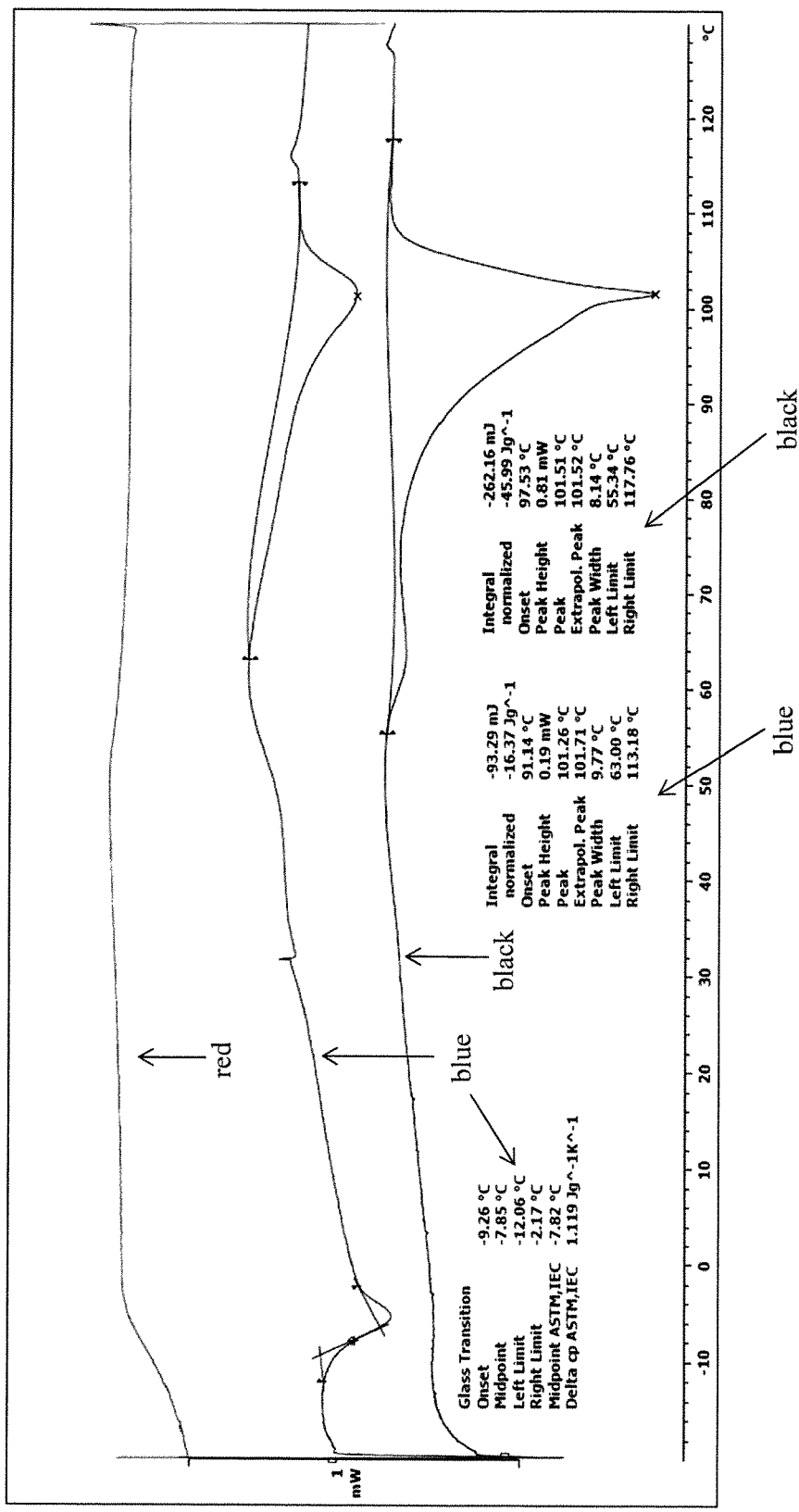
FIG. 25. Thermal properties of a stereocomplex formed from (S)- and (R)-poly(propylene succinate) of 70% enantiomeric excess. Black line is the first heat. Red line is cooling. Blue line is second heat.

FIG. 25 shows the stereocomplex formed from (S)- and (R)-poly(propylene succinate) of 70% enantiomeric excess. The first heat (in black) in this case shows a $T_m$ of 101° C., lower than that of the original stereocomplex and of the 80% enantiomeric excess stereocomplex, but again is still higher than (S)- or (R)-poly(propylene succinate) alone. Recrystallization again does not occur immediately upon cooling (in red), but still to some extent does occur during the second heat (in blue), around 64° C., slightly higher than in the 80% example, suggesting recrystallization time increases the lower the enantiopurity of the stereocomplex. Additionally, the enthalpy decreases from 55 J/g for the 80% example to 46 J/g.

Figure 26:
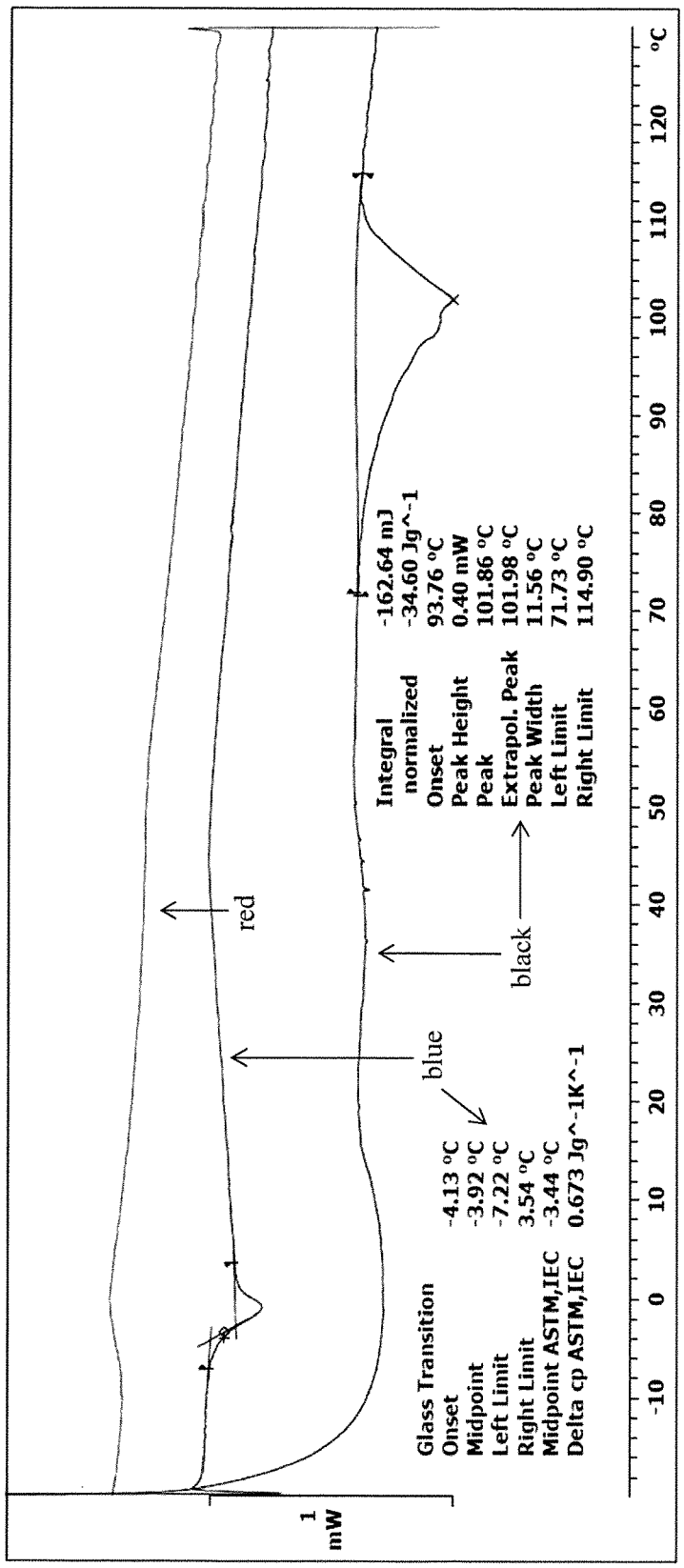
FIG. 26. Thermal properties of a stereocomplex formed from (S)- and (R)-poly(propylene succinate) of 60% enantiomeric excess. Black line is the first heat. Red line is cooling. Blue line is second heat.

Lastly, FIG. 26 shows the stereocomplex formed from (S)- and (R)-poly(propylene succinate) of 60% enantiomeric excess. The first heat (in black) in this case still shows a $T_m$ of 101° C., similar to the 70% example, but the enthalpy decreases from 46 J/g to 35 J/g, suggesting a lower amount of crystallinity in the stereocomplex. Recrystallization now does not occur immediately upon cooling (in red), or during the second heat (in blue).

These three stereocomplexes, formed from (S)- and (R)-poly(propylene succinate) of varying enantiopurity, demonstrate that stereocomplexation still occurs even if a large number of stereodefects are present in the parent polymers. Melting temperature and enthalpy both decrease (and recrystallization time increases) as the enantiopurity of the parent polymers decreases, but the composites still have improved thermal properties compared to the parent polymers.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A composition comprising:
   polymer chains that form one or more stereocomplexes, wherein the polymer chains comprise i) first enantiomeric polymer chains having a first enantiomeric structure that comprise individual repeat units having the following structure:

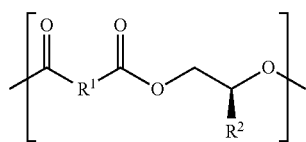

(Repeat Unit Structure I)

and
second enantiomeric polymer chains having a second enantiomeric structure that is the opposite absolute stereochemistry of the first enantiomeric structure that comprise individual repeat units having the following structure:

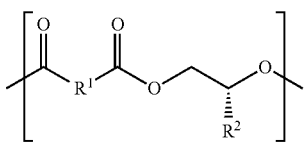

(Repeat Unit Structure II)

or
ii) individual repeat units having both Repeat Unit Structure I and Repeat Unit Structure II, and wherein $R^1$ is selected from —(CH$_2$)$_x$—, wherein x is 2-6, cis or trans —CR$^3$=CR$^4$—, wherein $R^3$ and $R^4$ are selected from —H, —CH$_3$, and —Cl, —CH$_2$C(=CH$_2$)—, ortho —C$_6$H$_4$—, —CH$_2$OCH$_2$—, 1,8-naphthylenediyl, and 3,4-cyclohexene-diyl,
$R^2$ is selected from —CH$_3$, —CF$_3$, C$_2$ to C$_8$ alkyl group or aryl group, —CH$_2$OR$^5$, wherein $R^5$ is a C$_2$ to C$_8$ alkyl group or aryl group, and —CH$_2$X, wherein X is Cl, Br, I, or F.

2. The composition of claim 1, wherein
95% or greater of the stereocenters in the individual repeat units of the first enantiomeric polymer chains have Repeat Unit Structure I,
95% or greater of the stereocenters in the individual repeat units of the second enantiomeric polymer chains have Repeat Unit Structure II,
the ratio of first enantiomeric polymer chains to second enantiomeric polymer is 1:19 to 19:1, the first enantiomeric polymer chains comprise 20 to 5000 individual repeat units of the Repeat Unit Structure I,
and the second enantiomeric polymer chains comprise 20 to 5000 individual repeat units of the Repeat Unit Structure II.

3. The composition of claim 1, wherein the ratio of first enantiomeric polymer chains to second enantiomeric polymer chains ranges from 1:9 to 9:1.

4. The composition of claim 1, wherein the first enantiomeric polymer chain and/or second enantiomeric polymer chain further comprises a small molecule and/or polymer chain covalently bound to the first enantiomeric polymer chain and/or second enantiomeric polymer chain.

5. The composition of claim 4, wherein one or more of the first enantiomeric polymer chains has the following structure:

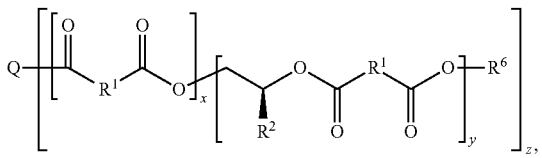

wherein x is 0 or 1, y is 10 to 5000, and z is 1 to 100, and/or
one or more of the second enantiomeric polymer chains has the following structure:

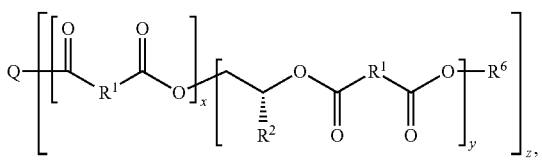

wherein x is 0 or 1, y is 10 to 5000, and z is 1 to 100,
$R^6$ is a C$_2$ to C$_8$ hydroxyalkyl group or hydrogen atom, and
Q is a polymeric chain or a small molecule and is attached to the enantiomeric polymer chain by an ester linkage.

6. The composition of claim 1, wherein
the first enantiomeric polymer chains are random copolymers comprising the following structure:

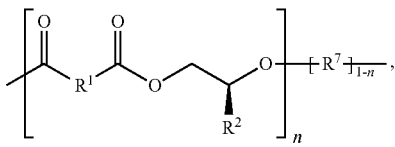

wherein n is 0.20 to 0.99, and
the second enantiomeric polymer chains are random copolymers comprising the following structure:

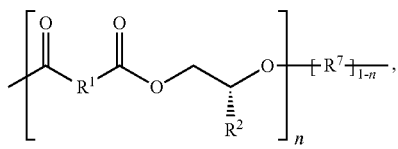

wherein n 0.20 to 0.99, the ratio of first enantiomeric polymer chains to second enantiomeric polymer chains is 1:19 to 19:1, and $R^7$ is —$CO_2R^8O$—, wherein $R^8$ is selected from $C_2$ to $C_8$ alkyl linker group or aryl linker group, —$CO(CH_2)_xO$—, wherein x is 2-5, —$COCHR^9O$—, wherein $R^9$ is a $C_2$ to $C_8$ alkyl group or aryl group, or —$CH_2CHR^{10}O$—, wherein $R^{10}$ is —$CH_3$, —$CF_3$, $C_2$ to $C_8$ alkyl group or aryl group, —$CH_2OR^{11}$, wherein $R^{11}$ is a $C_2$ to $C_8$ alkyl group or aryl group, and —$CH_2X$, wherein X is Cl, Br, I, or F.

7. The composition of claim 6, wherein the ratio of first enantiomeric polymer chains to second enantiomeric polymer chains is 1:9 to 9:1.

8. The composition of claim 1, wherein the first enantiomeric polymer chains are random copolymers comprising the following structure:

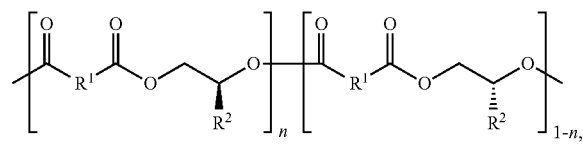

wherein n is 0.60 to 0.99 and the individual n repeat units have a first configuration and the individual 1-n repeat units has a second configuration that is the opposite absolute stereochemistry of the first configuration, the second enantiomeric polymer chains are random copolymers comprising the following structure:

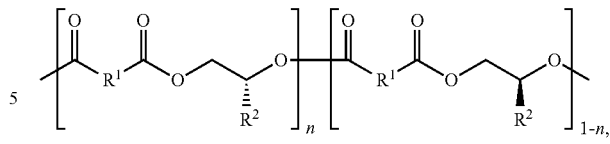

wherein n is 0.60 to 0.99 of the composition and the individual n repeat units have a first configuration and the individual 1-n repeat units have a second configuration that is the opposite absolute stereochemistry of the first configuration, and the ratio of first enantiomeric polymer chains to second enantiomeric polymer chains is 1:19 to 19:1.

9. The composition of claim 8, wherein the ratio of first enantiomeric polymer chains to second enantiomeric polymer chains is 1:9 to 9:1.

10. The composition of claim 1, wherein the enantiomeric polymer chains are stereoblock copolymers of the following structure:

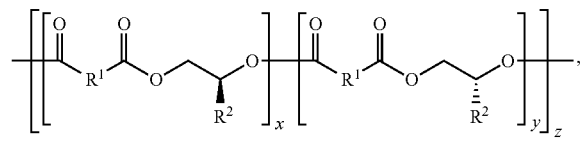

wherein x is 10 to 1000 and y is 10 to 1000 and z is 1 to 100, the ratio of x and y is 1:19 to 19:1.

11. An article of manufacture comprising the composition of claim 1.

12. The article of manufacture of claim 11, wherein the article of manufacture is a packaging material, disposable tableware, an agricultural film, loose-fill packaging, a compost bag, upholstery, or a disposable garment.

13. The article of manufacture of claim 1, wherein the article of manufacture is a biomedical device, a drug delivery device, an awning, a feminine hygiene product, a diaper, or a component thereof.

* * * * *

UNITED STATES PATENT AND TRADEMARK OFFICE
CERTIFICATE OF CORRECTION

PATENT NO. : 10,377,850 B2
APPLICATION NO. : 15/502234
DATED : August 13, 2019
INVENTOR(S) : Coates et al.

It is certified that error appears in the above-identified patent and that said Letters Patent is hereby corrected as shown below:

In the Claims

Column 28, Line 37, in Claim 13:
"of claim 1"
Should read:
--of claim 11--.

Signed and Sealed this
Twenty-second Day of October, 2019

Andrei Iancu
*Director of the United States Patent and Trademark Office*